United States Patent [19]

Haino et al.

[11] Patent Number: 5,089,366
[45] Date of Patent: Feb. 18, 1992

[54] HYDRAZONE COMPOUND IN AN ELECTROPHOTOGRAPHIC RECEPTOR

[75] Inventors: Kozo Haino; Akira Itoh; Makoto Okaji; Kazuhiro Emoto; Tatsuya Kodera; Kazuchiyo Takaoka, all of Tsukuba, Japan

[73] Assignee: Mitsubishi Paper Mills Limited, Tokyo, Japan

[21] Appl. No.: 463,033

[22] Filed: Jan. 3, 1990

[30] Foreign Application Priority Data

| Jan. 9, 1989 | [JP] | Japan | 1-003345 |
| Jan. 10, 1989 | [JP] | Japan | 1-003966 |
| Jan. 10, 1989 | [JP] | Japan | 1-003969 |
| Jan. 11, 1989 | [JP] | Japan | 1-005193 |
| Jan. 13, 1989 | [JP] | Japan | 1-006648 |
| Mar. 31, 1989 | [JP] | Japan | 1-081269 |

[51] Int. Cl.$^5$ .................................. G03G 5/047
[52] U.S. Cl. .................................. 430/59; 430/49; 430/73
[58] Field of Search .................. 430/59, 73, 74

[56] References Cited

U.S. PATENT DOCUMENTS

| 4,420,548 | 12/1983 | Sakai et al. | 430/59 |
| 4,567,126 | 1/1986 | Emoto et al. | 430/59 |
| 4,839,252 | 6/1989 | Murate et al. | 430/74 |

FOREIGN PATENT DOCUMENTS

| 3329054 | 7/1983 | Fed. Rep. of Germany |
| 3201202 | 2/1984 | Fed. Rep. of Germany |

OTHER PUBLICATIONS

Official Action of the German Patent Office, dated Apr. 29, 1991.

English Translation of the Official Action of the German Patent Office (dated Apr. 29, 1991).

Primary Examiner—John Goodrow
Attorney, Agent, or Firm—Cushman, Darby & Cushman

[57] ABSTRACT

Disclosed is an electrophotographic photoreceptor which is high in sensitivity and endurance and which comprises an electroconductive support and, provided thereon, a photosensitive layer which contains a hydrozone compound represented by the following formula [I], [II], or [III]:

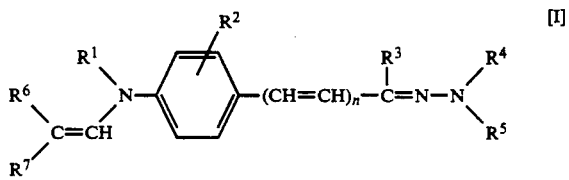

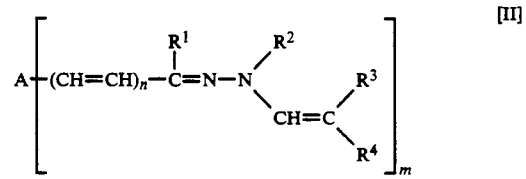

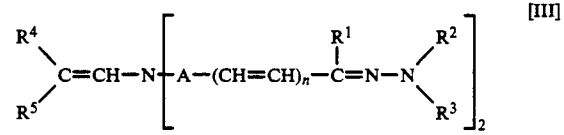

wherein the various subgroups designated by R or A are as described in the specification.

9 Claims, 1 Drawing Sheet

HYDRAZONE COMPOUND IN AN ELECTROPHOTOGRAPHIC RECEPTOR

BACKGROUND OF THE INVENTION

The present invention relates to an electrophotographic photoreceptor which contains a novel hydrazone compound.

Hitherto, inorganic photoconductive substances such as selenium, cadmium sulfide, zinc oxide and silicon have been known for photoreceptors of electrophotogarphic system and widely studied and some of them have been put to practical use. Recently, organic photoconductive materials have also been intensively studied as electrophotographic photoreceptors and some of them have been practically used.

In general, inorganic materials are unsatisfactory, for example, selenium materials have problems such as deterioration in heat stability and characteristics due to crystallization and difficulty in production and cadmium sulfide materials have problems in moisture resistance, endurance and disposal of industrial waste. On the other hand, organic materials have advantages such as good film-formability, excellent flexibility, light weight, high transparency and easy designing of photoreceptors for wavelength of wide region by suitable sensitization. Thus, organic materials have increasingly attracted public attention.

Photoreceptors used in electrophotographic technique are required to possess the following fundamental properties, namely, (1) high chargeability for corona discharge in the dark place, (2) less leakage of the resulting charge in the dark place (dark decay), (3) rapid release of charge by irradiation with light (light decay), and (4) less residual charge after irradiation with light.

Extensive research has been made on photoconductive polymers as organic photoconductive substances including polyvinylcarbazole, but these are not necessarily sufficient in film-formability, flexibility and adhesion and besides these cannot be said to have sufficiently possess the above-mentioned fundamental properties as photoreceptor.

On the other hand, in case of organic low molecular photoconductive compounds, photoreceptors excellent in film-formability, adhesion, flexibility and other mechanical strength can be obtained therefrom by selection of binders and others used for formation of photoreceptors, but it is difficult to find compounds suitable to keep the characteristic of high sensitivity.

In order to improve these problems, there has been made development of organic photoreceptors having higher sensitivity by bearing the carrier generating function and the carrier transporting function by different substances. Characteristic of such photoreceptor called double-layered structure is that materials suitable for respective functions can be selected from wide variety of materials and photoreceptors having optional performances can be easily produced and thus intensive research has been made on such photoreceptors.

As explained above, many improvements have been made in production of electrophotographic photoreceptors, but those which meet the requirements for fundamental properties mentioned above and high endurance have not yet been obtained.

SUMMARY OF THE INVENTION

The object of the present invention is to provide an electrophotographic photoreceptor having high sensitivity and high endurance and especially to provide an electrophotographic photoreceptor which is high in charge characteristics, shows substantially no reduction of sensitivity after repeated use and is stable in charge potential.

DESCRIPTION OF THE INVENTION

Figure 1:
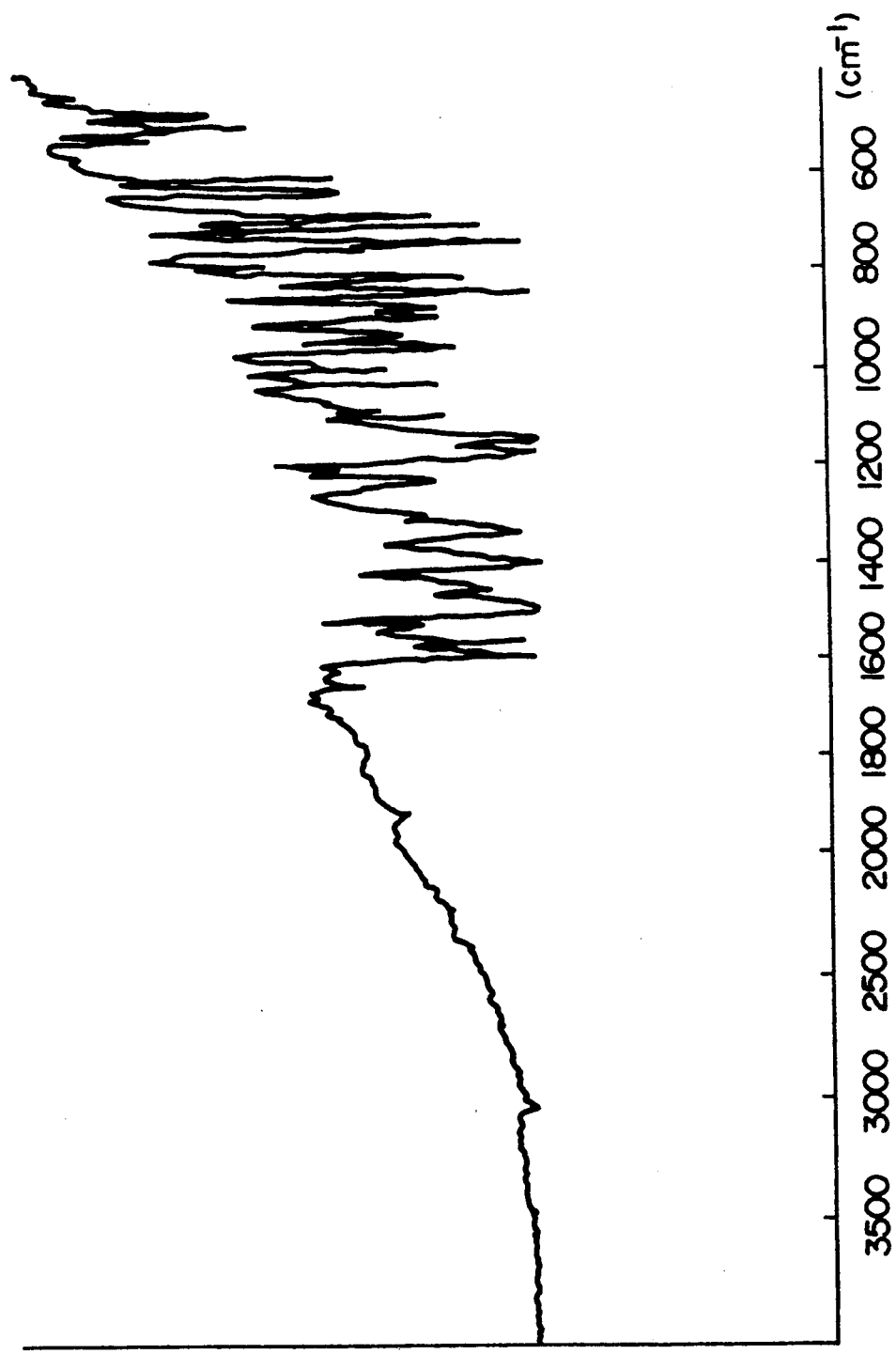
FIG. 1 shows infrared absorption spectrum of compound I-(4) exemplified hereinafter.

As a result of research conducted by the inventors on photoconductive substances having high sensitivity and high endurance, it has been found that the novel hydrazone compounds represented by the formula [I], [II], and [III] are effective and the present invention has been accomplished.

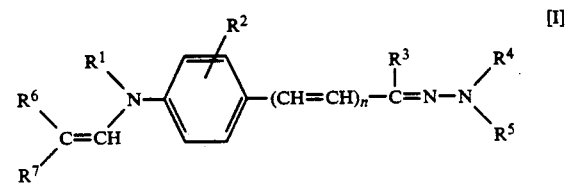

(wherein $R^1$ represents an alkyl group which may have substituent, an aralkyl group which may have substituent, an aryl group which may have substituent, a hetrocyclic ring group which may have substituent or an atom group necessary to form a ring together with nitrogen atom carrying $R^1$ and carbon atom in the ortho position of the benzene ring in respect to said nitrogen atom; $R^2$ represents a hydrogen atom, an alkyl group which may have substituent or an alkoxy group which may have substituent; $R^3$ represents a hydrogen atom, an alkyl group which may have substituent or an aryl group which may have substituent; $R^4$ represents an alkyl group which may have substituent, an aralkyl group which may have substituent or an aryl group which may have substituent; $R^5$ represents an alkyl group which may have substituent, an aralkyl group which may have substituent, an aryl group which may have substituent or an alkenyl group which may have substituent; $R^6$ and $R^7$ which may be identical or different each represents a hydrogen atom, an alkyl group which may have substituent, an aralkyl group which may have substituent or an aryl group which may have substituent and $R^6$ and $R^7$ may link to each other to form a ring; and n is 0 or 1).

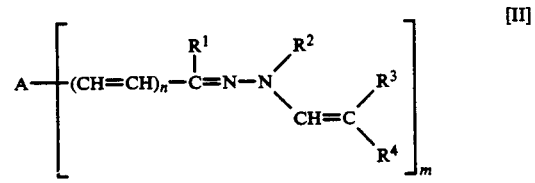

(wherein A represents an aromatic ring or a heterocyclic ring, $R^1$ represents a hydrogen atom, an alkyl group which may have substituent or an aryl group which may have substituent; $R^2$ represents an alkyl group which may have substituent, an aralkyl group which may have substituent or an aryl group which may have substituent; $R^3$ and $R^4$ which may be identical or different each represents a hydrogen atom, an alkyl group which may have substituent, an aralkyl group which may have substituent or an aryl group which may have substituent and $R^3$ and $R^4$ may link to each other to form a ring; m is 1 or 2; and n is 0 or 1).

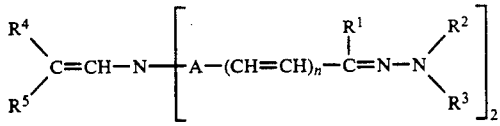

(wherein A represents an aromatic ring and the two A may link through a bond, an atom or a group of atoms to form a heterocyclic ring together with nitrogen atom, $R^1$ represents a hydrogen atom, an alkyl group which may have substituent or an aryl group which may have substituent; $R^2$ and $R^3$ which may be identical or different each represents an alkyl group which may have substituent, an aralkyl group which may have substituent or an aryl group which may have substituent; $R^4$ and $R^5$ which may be identical or different each represents a hydrogen atom, an alkyl group which may have substituent, an aralkyl group which may have substituent or an aryl group which may have substituent and $R^4$ and $R^5$ may link to each other to form a ring; and n is 0 or 1).

Examples of the substituent $R^1$ in the formula [I] are alkyl groups such as methyl, ethyl, propyl and butyl; aralkyl groups such as benzyl, $\beta$-phenylethyl, p-methylbenzyl, p-methoxybenzyl, and $\alpha$-naphthylmethyl; aryl groups such as phenyl, naphthyl, tolyl, xylyl, chlorophenyl, methoxyphenyl and methylnaphthyl; heterocyclic rings such as pyridine ring, quinoline ring, thiophene ring, and benzothiophene ring; and carbazole ring, phenoxazine ring, phenothiazine ring and tetrahydroquinoline ring as rings which $R^1$ forms together with nitrogen atom and carbon atom in the ortho position of benzene ring in respect to said nitrogen atom.

Examples of the substituent $R^2$ in the formula [I] are alkyl groups such as methyl, ethyl and propyl; and alkoxy groups such as methoxy, ethoxy and propoxy.

Examples of the substituent $R^3$ in the formula [I] are hydrogen atom; alkyl groups such as methyl, ethyl and propyl; and aryl groups such as phenyl, tolyl, methoxyphenyl and chlororphenyl.

Examples of the substituent $R^4$ in the formula [I] are alkyl groups such as methyl, ethyl, propyl and butyl; aralkyl groups such as benzyl, $\beta$-phenylethyl, chlorobenzyl, methylbenzyl, methoxybenzyl, and $\alpha$-naphthylmethyl; and aryl groups such as phenyl, naphthyl, methoxyphenyl, ethoxyphenyl, tolyl, xylyl and chlorophenyl.

Examples of the substituent $R^5$ in the formula [I] are alkyl groups such as methyl, ethyl, propyl and butyl; aralkyl groups such as benzyl, $\beta$-phenylethyl, chlorobenzyl, methylbenzyl, methoxybenzyl, and $\alpha$-naphthylmethyl; and aryl groups such as phenyl, naphthyl, methoxyphenyl, ethoxyphenyl, tolyl, xylyl and chlorophenyl; and alkenyl groups represented by

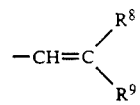

wherein $R^8$ and $R^9$ which may be identical or different each represents a hydrogen atom; alkyl groups such as methyl, ethyl propyl; aralkyl groups such as benzyl and $\beta$-phenylethyl; and aryl groups such as phenyl, methoxyphenyl, ethoxyphenyl, tolyl, xylyl and chlorophenyl; and $R^8$ and $R^9$ may link to each other to form a ring.

Examples of $R^6$ and $R^7$ in the formula [I] are hydrogen atom; alkyl groups such as methyl, ethyl and propyl; aralkyl groups such as benzyl and p-methylbenzyl; and aryl groups such as phenyl and p-methoxphenyl.

Examples of A in the formula [II] are aromatic rings such as benzene ring and naphthalene ring and heterocyclic rings such as carbazole ring and phenothiazine ring.

Examples of the substituent $R^1$ in the formula [II] are hydrogen atom; alkyl groups such as methyl, ethyl and propyl; and aryl groups such as phenyl, tolyl, methoxyphenyl and chlorophenyl.

Examples of the substituent $R^2$ in the formula [II] are alkyl groups such as methyl, ethyl, propyl and butyl; aralkyl groups such as benzyl, $\beta$-phenylethyl, chlorobenzyl, methylbenzyl, methoxybenzyl and $\alpha$-naphthylmethyl; and aryl groups such as phenyl, naphthyl, methoxyphenyl, ethoxyphenyl, tolyl, xylyl and chlorophenyl.

Examples of the substituents $R^3$ and $R^4$ are hydrogen atom; alkyl groups such as methyl and ethyl; aralkyl groups such as benzyl and p-methylbenzyl; and aryl groups such as phenyl and p-methoxyphenyl.

Examples of A in the formula [III] are aromatic rings such as benzene ring and naphthalene ring and heterocyclic rings formed together with nitrogen atom such as carbazole ring and phenothiazine ring.

Examples of the substituent $R^1$ in the formula [III] are hydrogen atom; alkyl groups such as methyl, ethyl and propyl; and aryl groups such as phenyl, tolyl, methoxyphenyl and chlorophenyl.

Examples of the substituent $R^2$ and $R^3$ in the formula [III] are alkyl groups such as methyl, ethyl, propyl and butyl; aralkyl groups such as benzyl, $\beta$-phenylethyl, chlorobenzyl, methylbenzyl, methoxybenzyl and $\alpha$-naphthylmethyl; and aryl groups such as phenyl, naphthyl, methoxyphenyl, ethoxyphenyl, tolyl, xylyl and chlorophenyl.

Examples of the substituent $R^4$ and $R^5$ in the formula [III] are hydrogen atom; alkyl groups such as methyl and ethyl; aralkyl groups such as benzyl and p-methylbenzyl; and aryl groups such as phenyl and p-methoxyphenyl.

The following are nonlimiting examples of hydrazone compounds represented by the formulas [I], [II], and [III] of the present invention.

Compounds represented by the formula [I]:

I-(1)
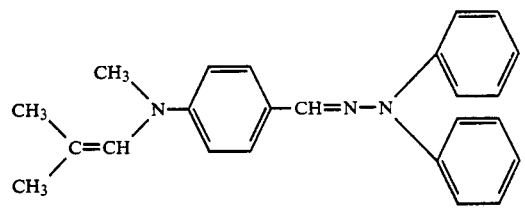
I-(2)
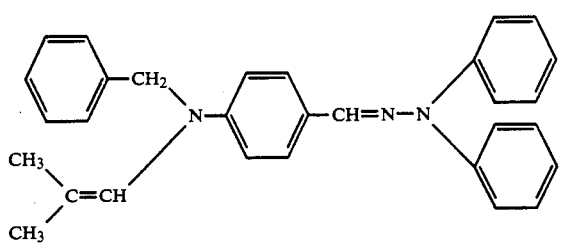
I-(3)
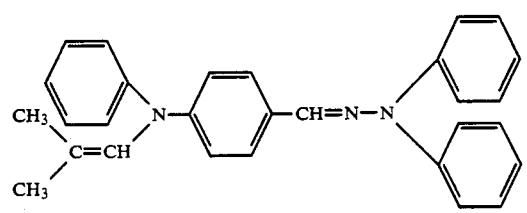
I-(4)
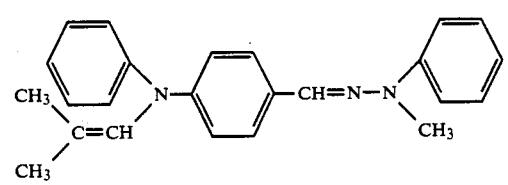
I-(5)
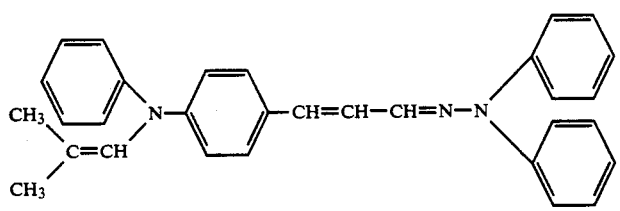
I-(6)
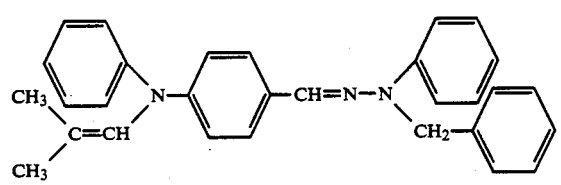
I-(7)
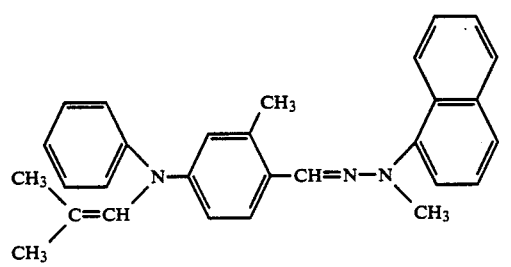

-continued
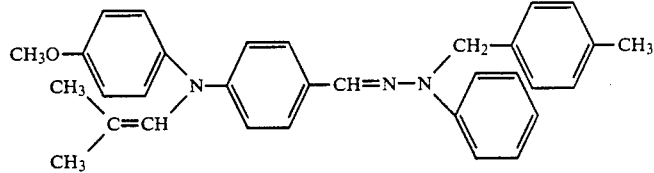
I-(8)
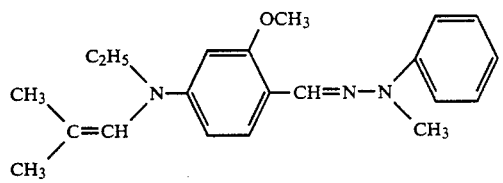
I-(9)
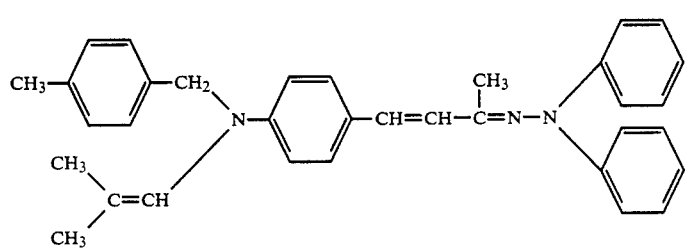
I-(10)
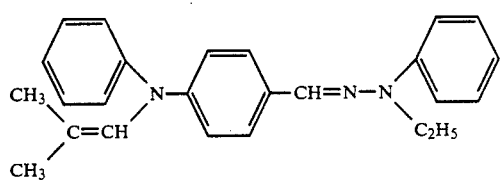
I-(11)
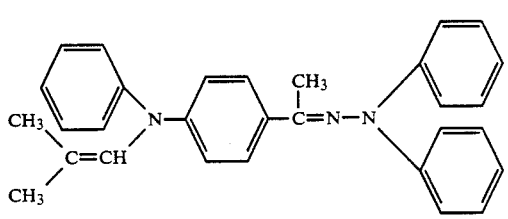
I-(12)
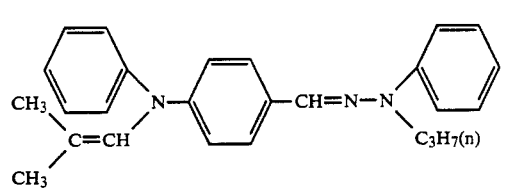
I-(13)
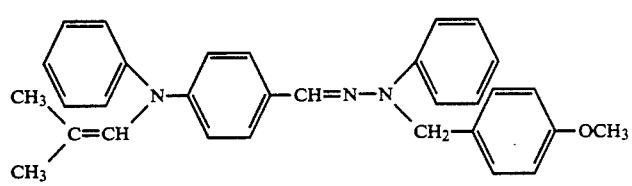
I-(14)
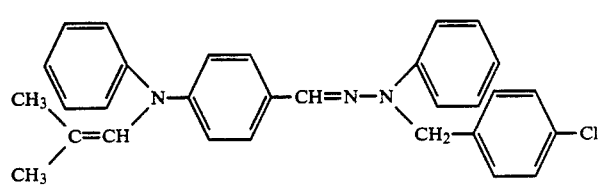
I-(15)

-continued
I-(16)
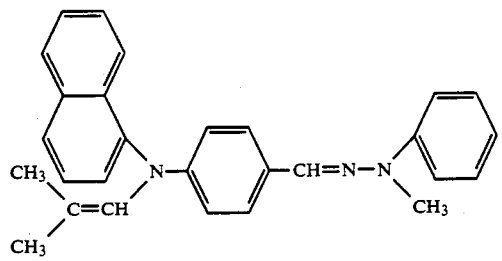
I-(17)
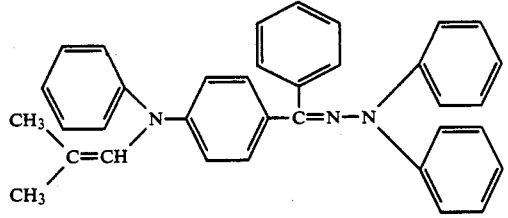
I-(18)
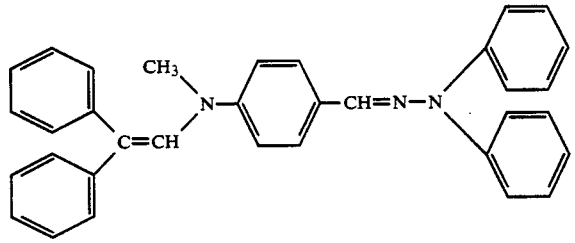
I-(19)
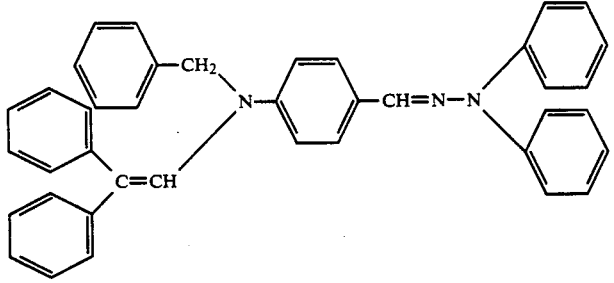
I-(20)
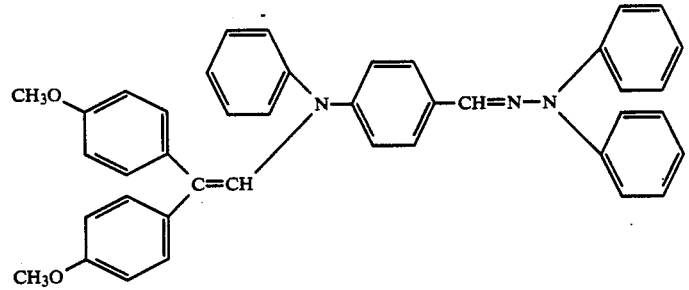
I-(21)
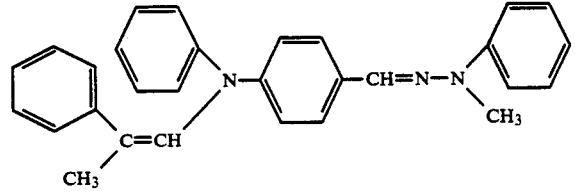

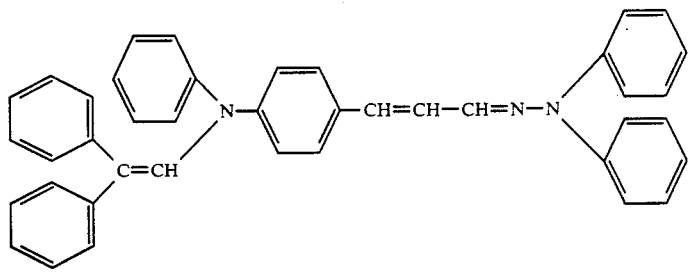
I-(22)
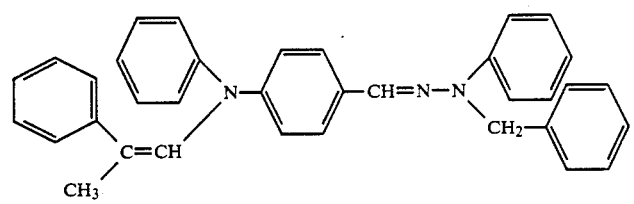
I-(23)
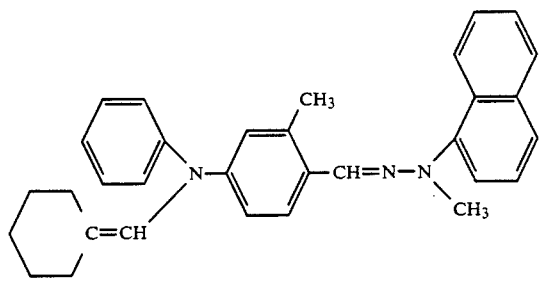
I-(24)
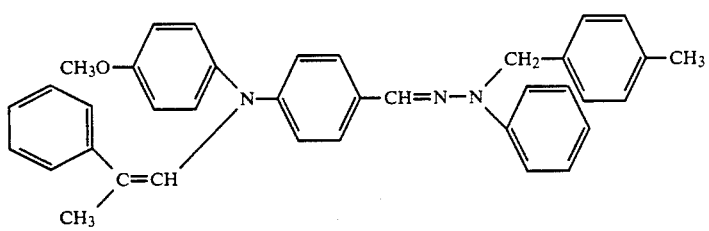
(I-(25)
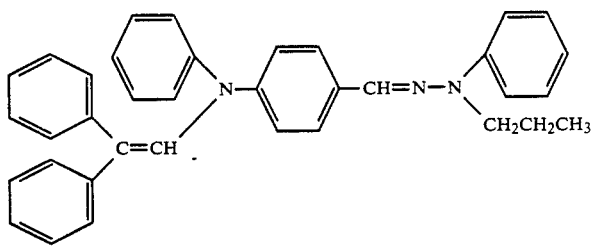
I-(26)
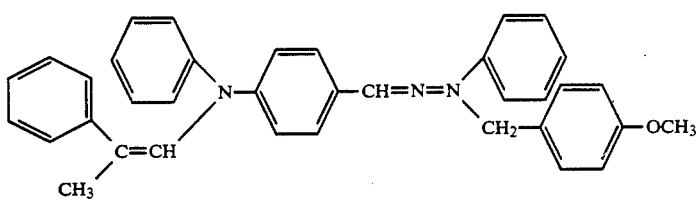
I-(27)
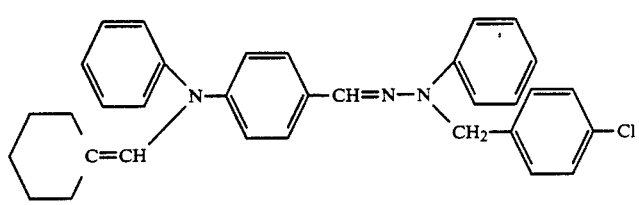
I-(28)

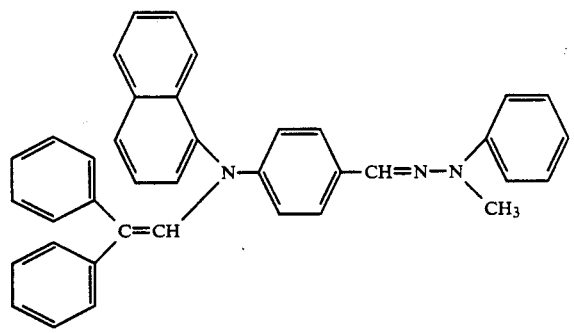
I-(29)
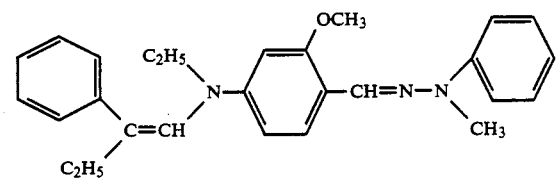
I-(30)
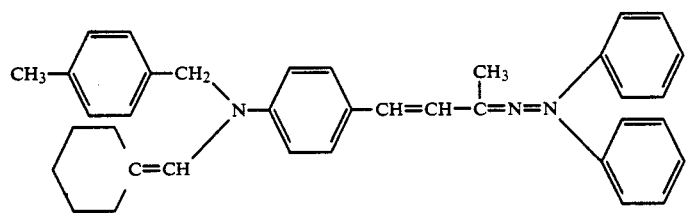
I-(31)
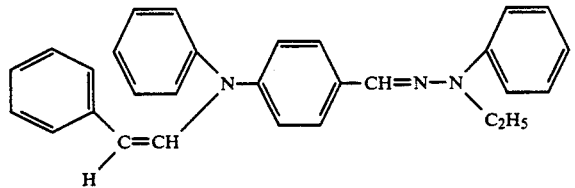
I-(32)
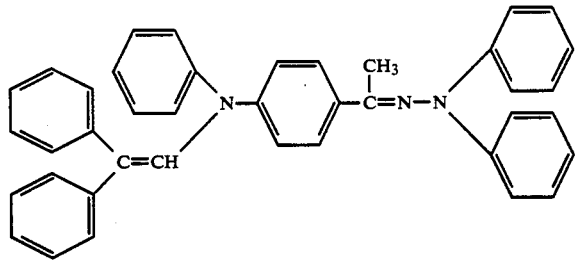
I-(33)
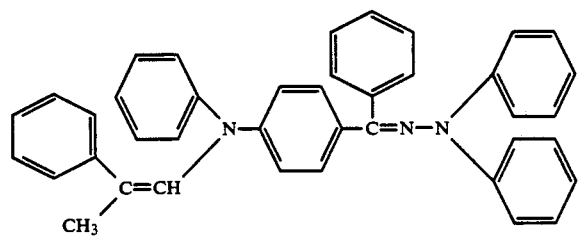
I-(34)

-continued
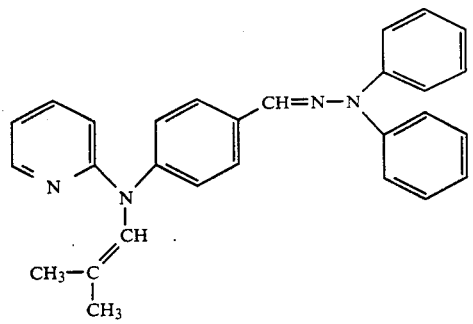
I-(35)
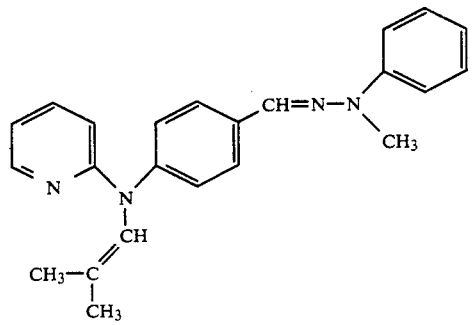
I-(36)
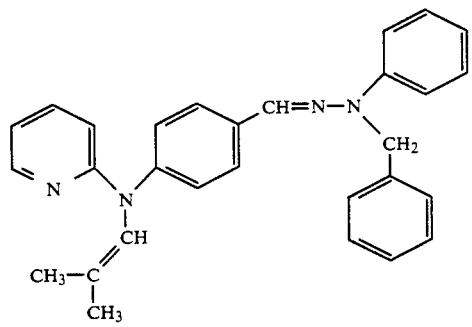
I-(37)
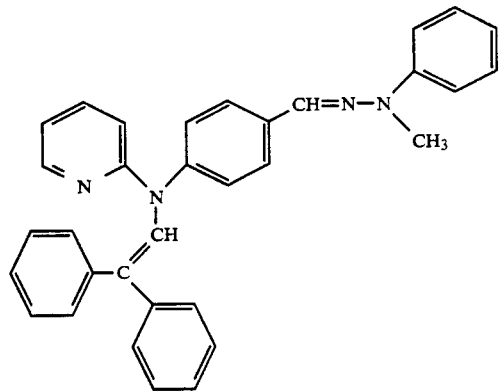
I-(38)

-continued
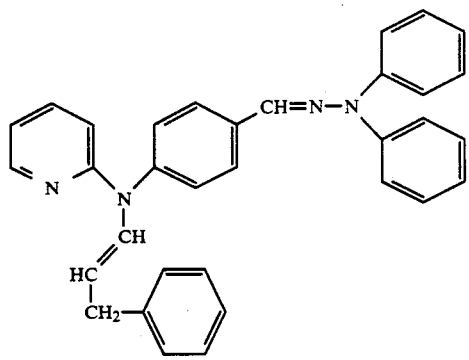
I-(39)
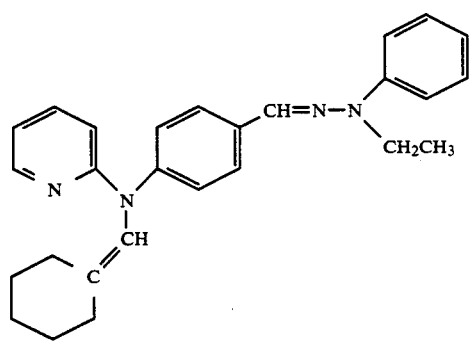
I-(40)
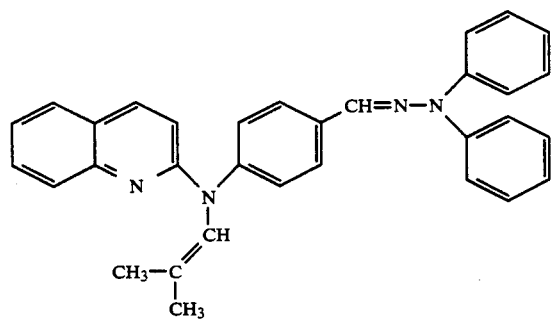
I-(41)
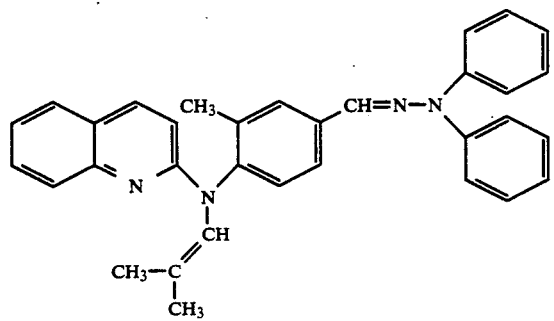
I-(42)

I-(43)
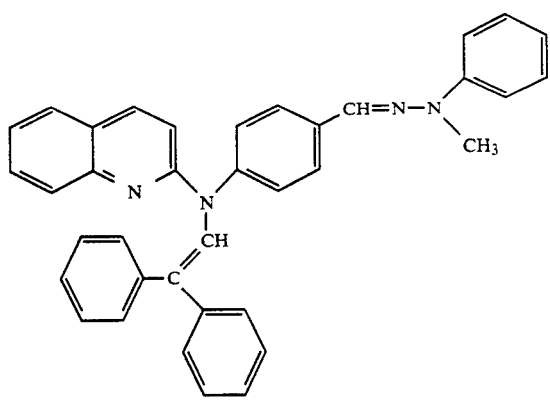
I-(44)
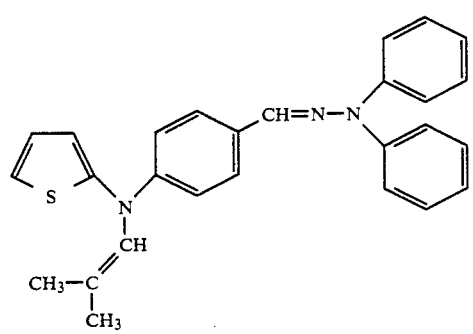
I-(45)
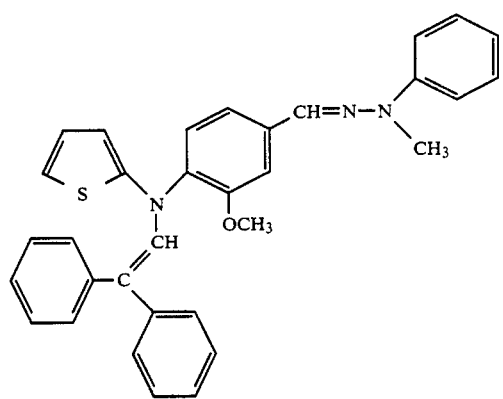
I-(46)
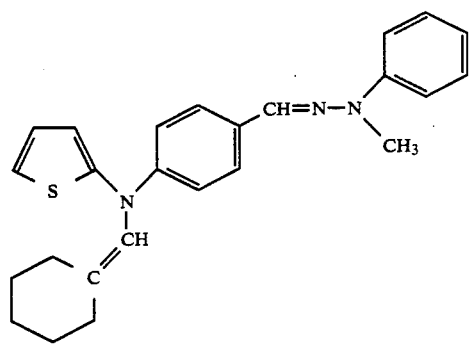

-continued
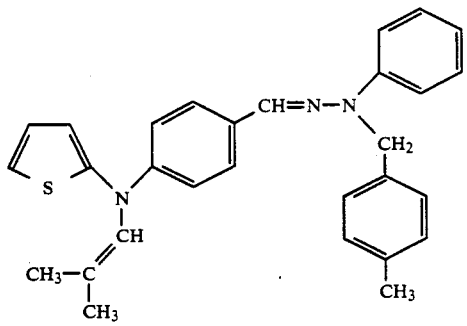
I-(47)
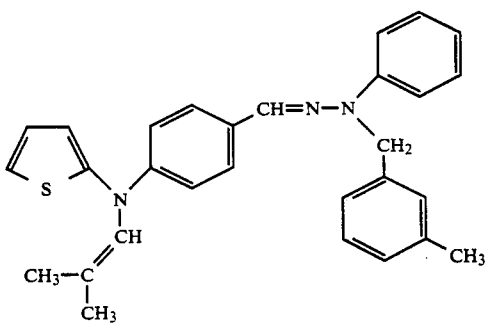
I-(48)
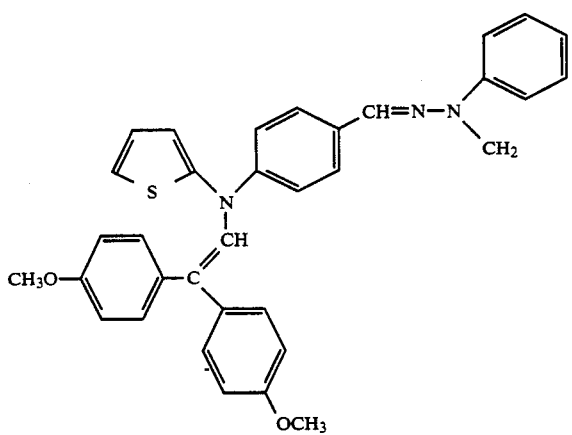
I-(49)
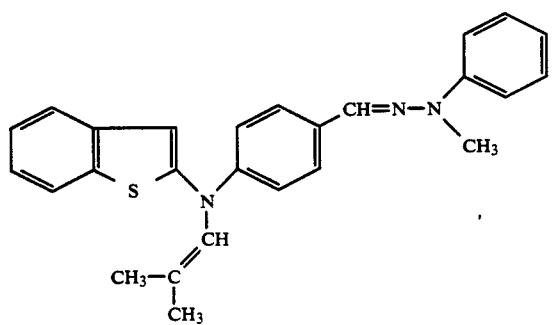
I-(50)

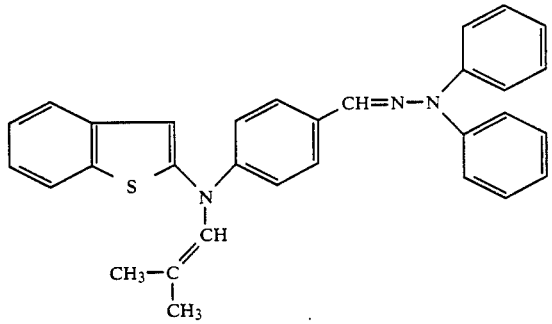
I-(51)
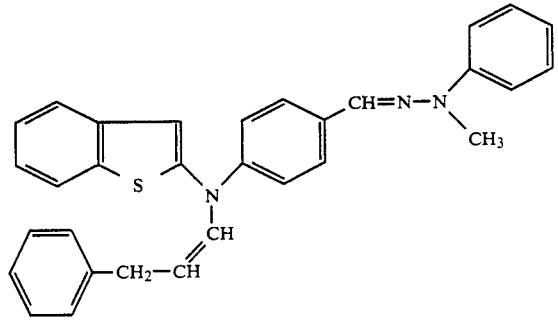
I-(52)
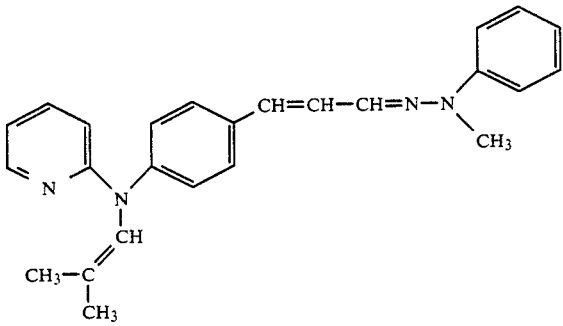
I-(53)
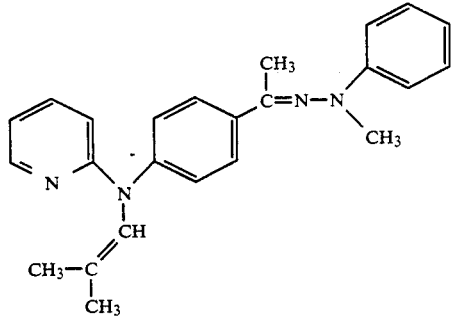
I-(54)
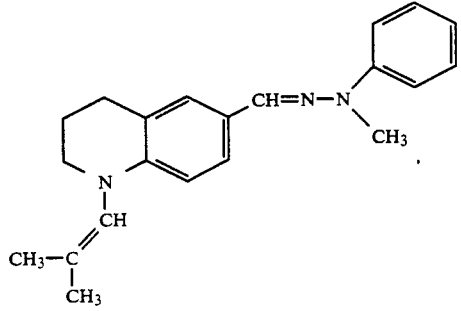
I-(55)

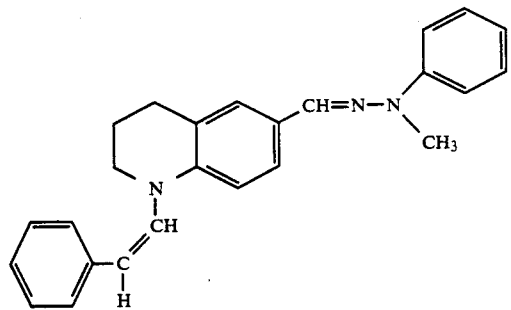
I-(56)
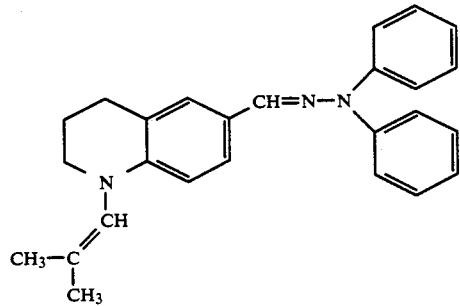
I-(57)
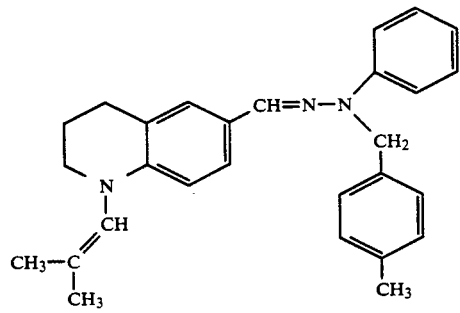
I-(58)
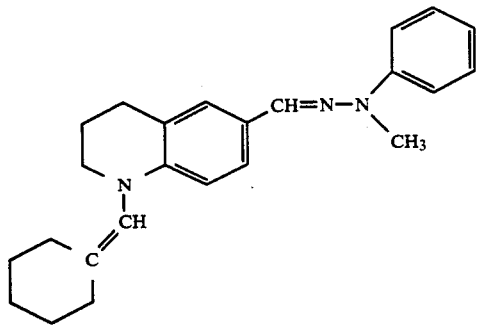
I-(59)
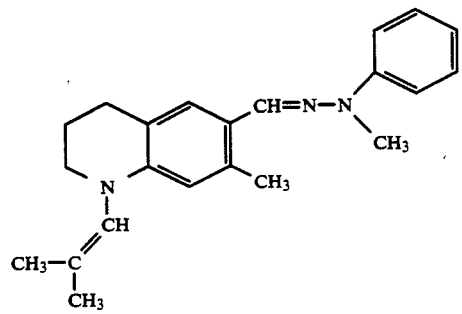
I-(60)

I-(61)
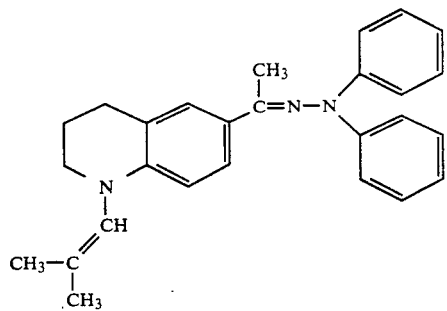
I-(62)
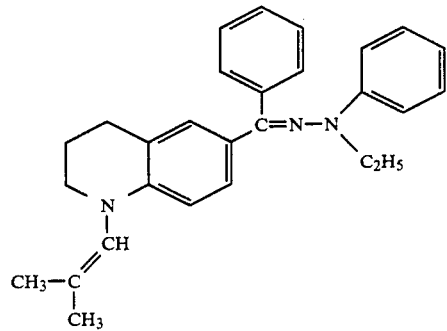
I-(63)
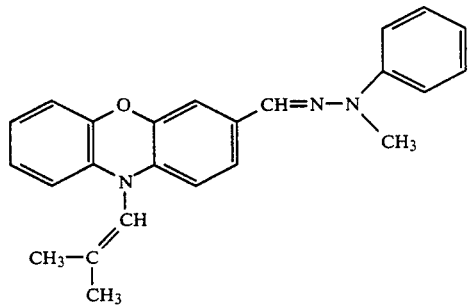
I-(64)
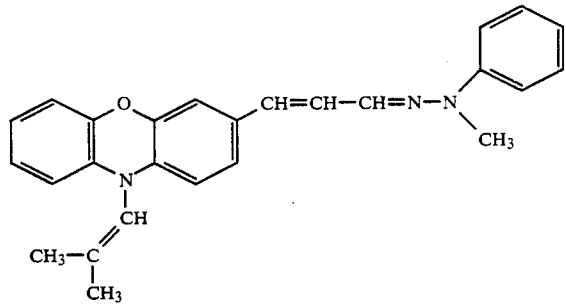
I-(65)
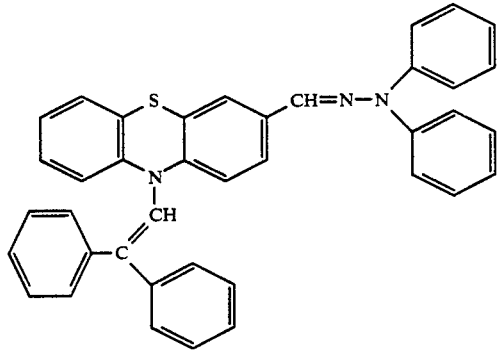

-continued
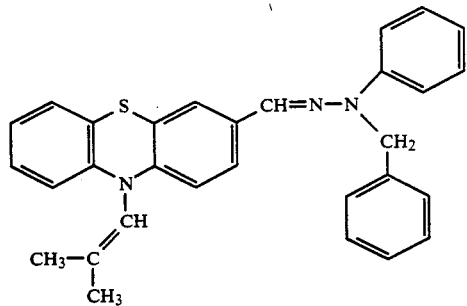 I-(66)
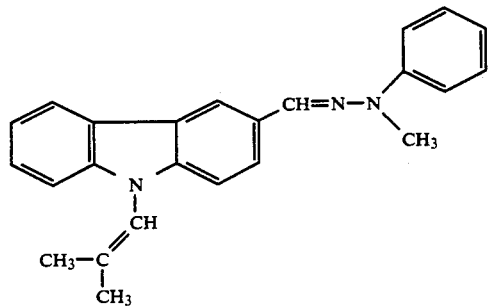 I-(67)
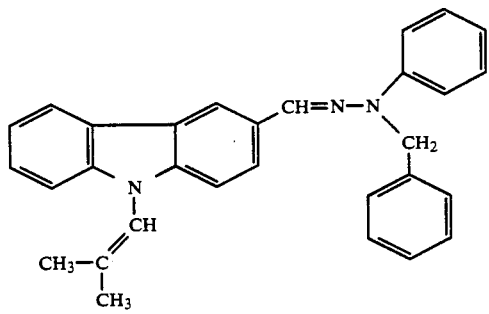 I-(68)
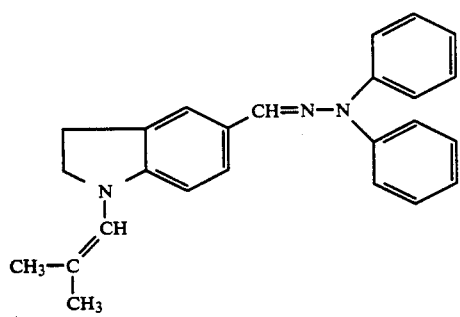 I-(69)
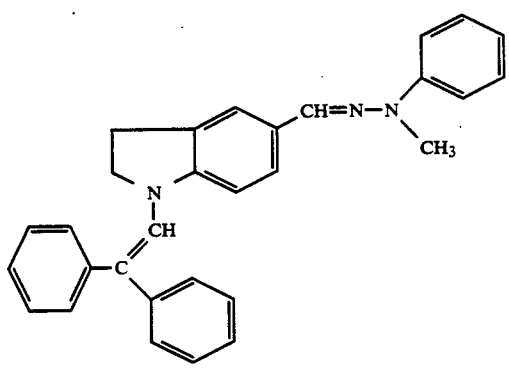 I-(70)

I-(71)
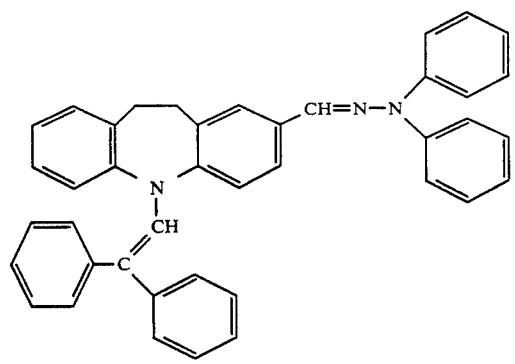
I-(72)
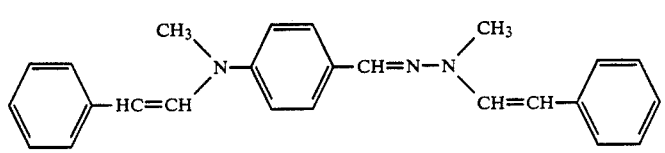
I-(73)
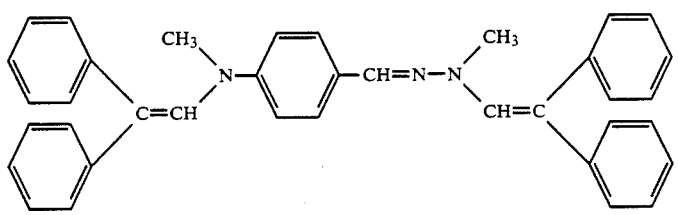
I-(74)
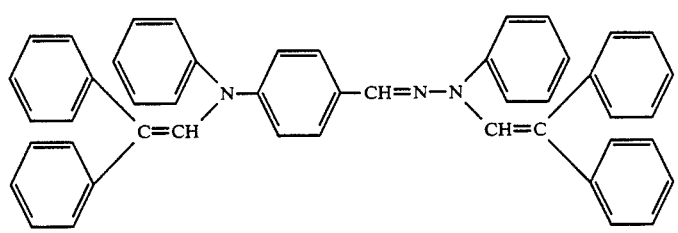
I-(75)
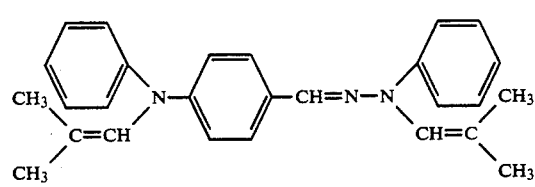
I-(76)
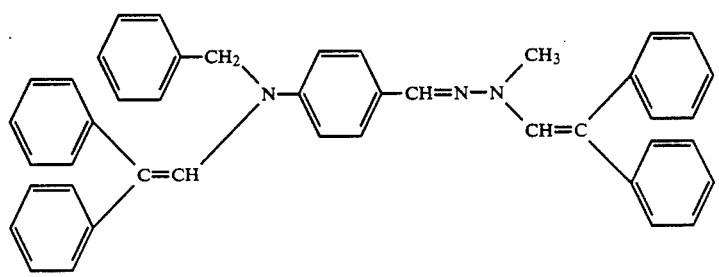

I-(77)
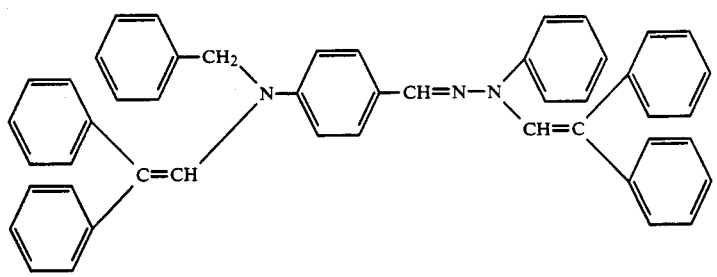
I-(78)
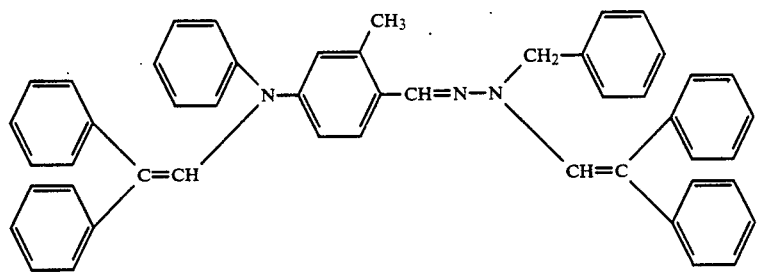
I-(79)
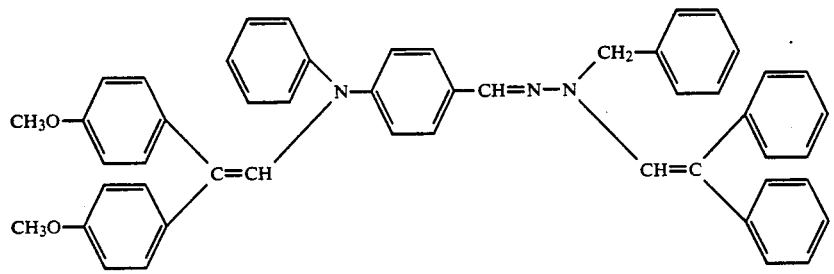
I-(80)
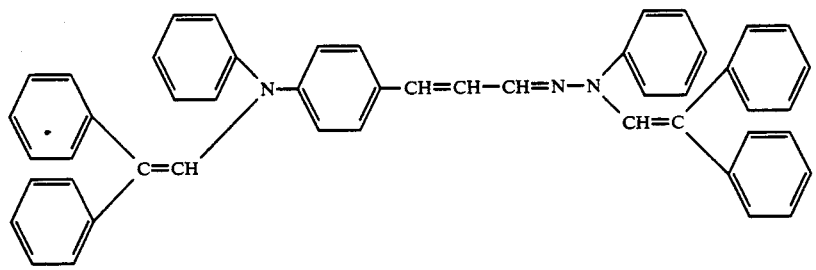
I-(81)
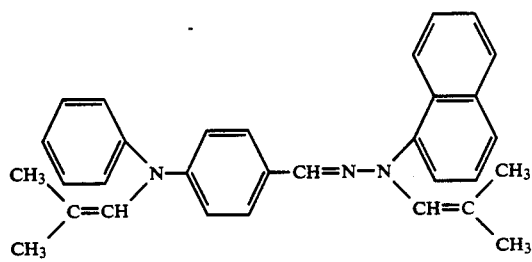
I-(82)
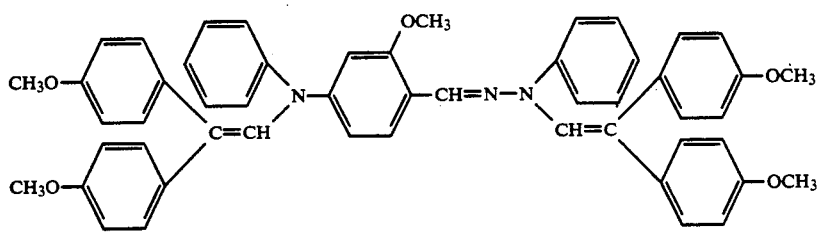

-continued
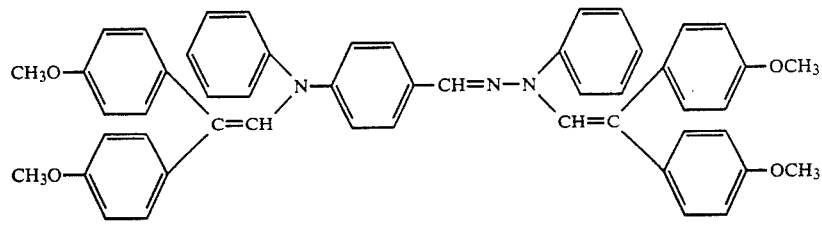
I-(83)
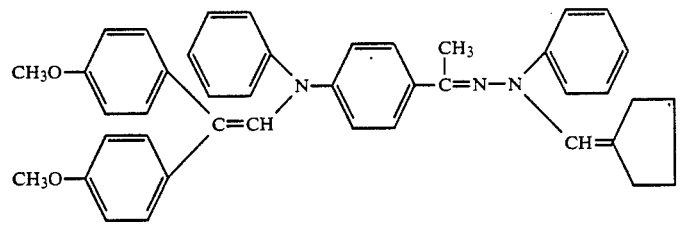
I-(84)
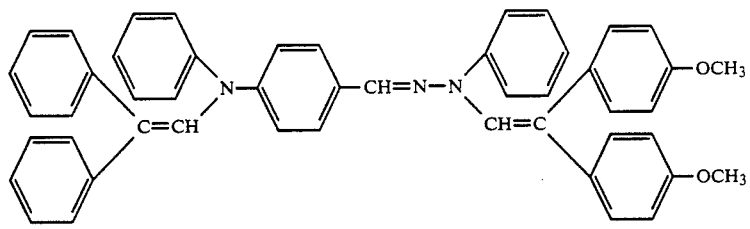
I-(85)
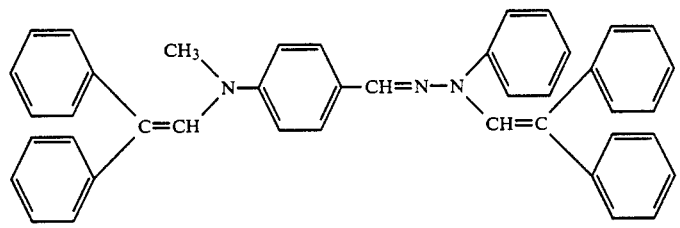
I-(86)
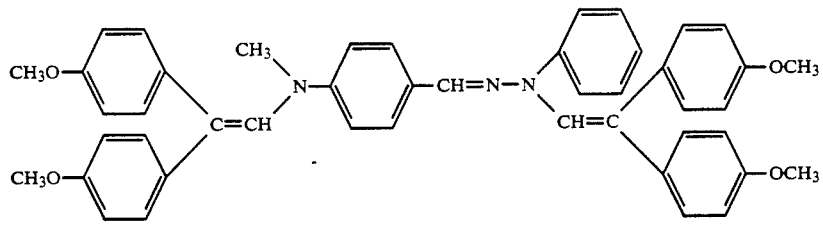
I-(87)
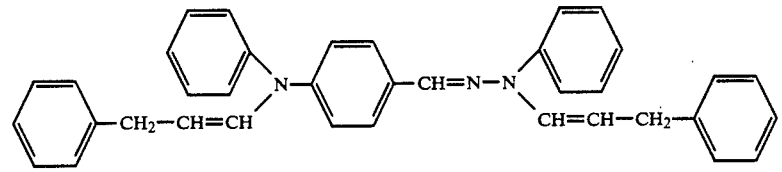
I-(88)
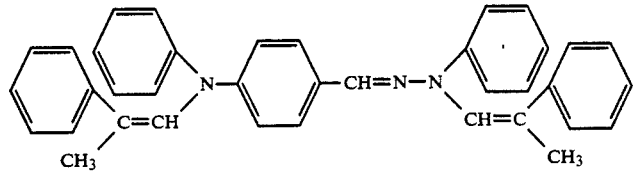
I-(89)

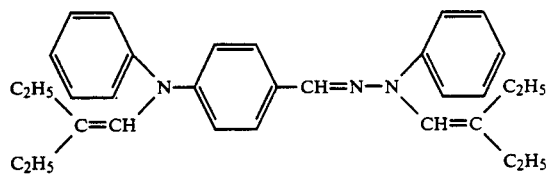
I-(90)
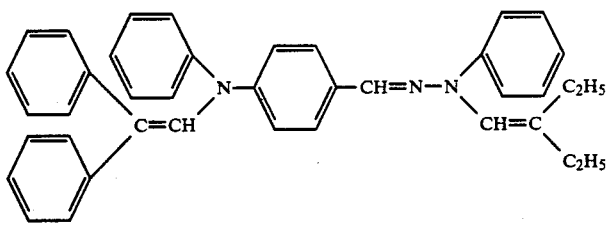
I-(91)
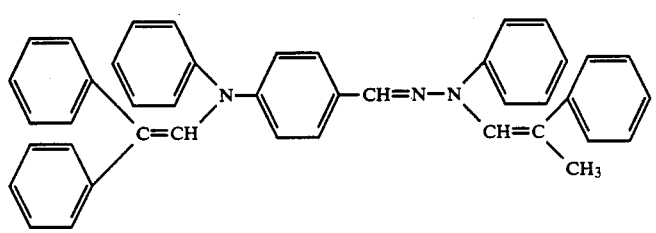
I-(92)
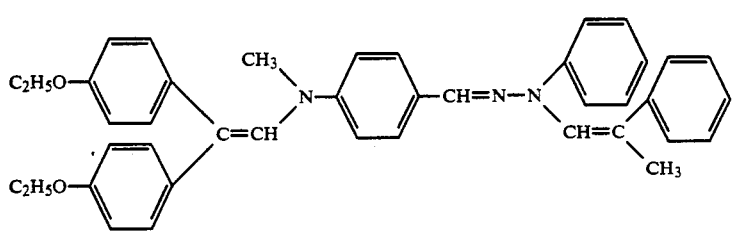
I-(93)
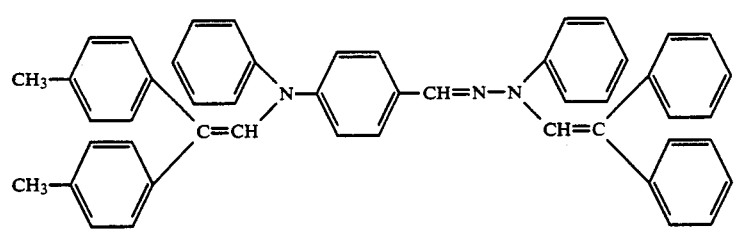
I-(94)
Compounds represented by formula [II]:
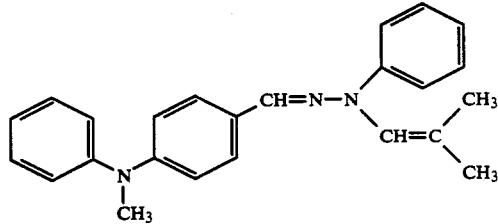
II-(1)

II-(2)
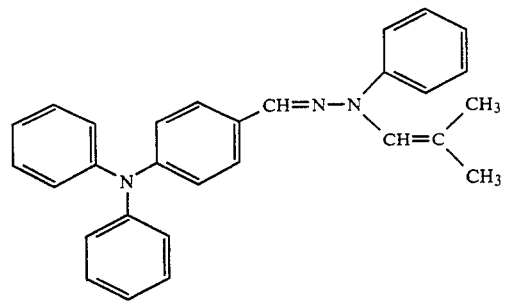
II-(3)
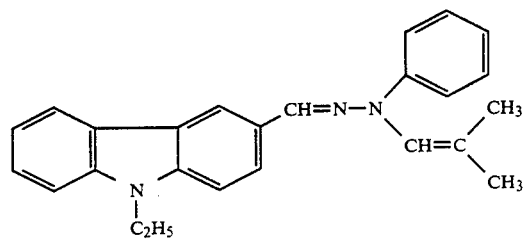
II-(4)
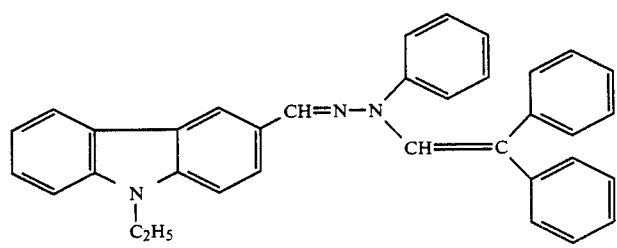
II-(5)
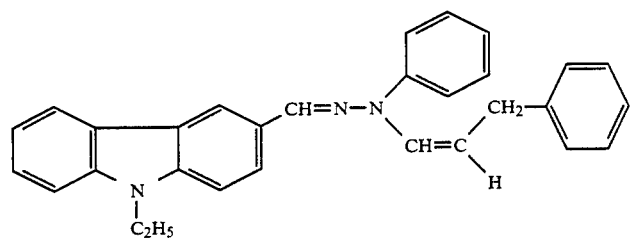
II-(6)
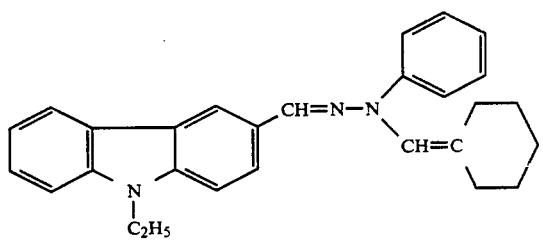
II-(7)
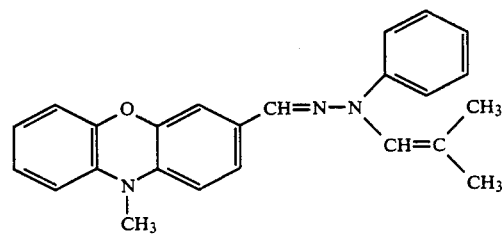

-continued
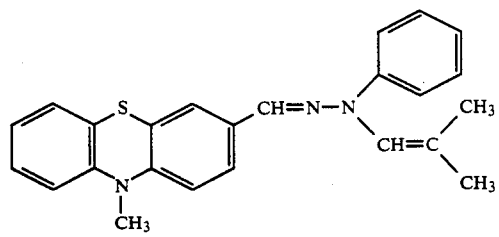
II-(8)
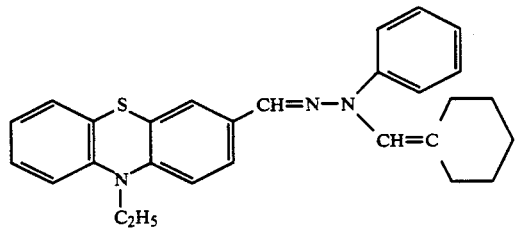
II-(9)
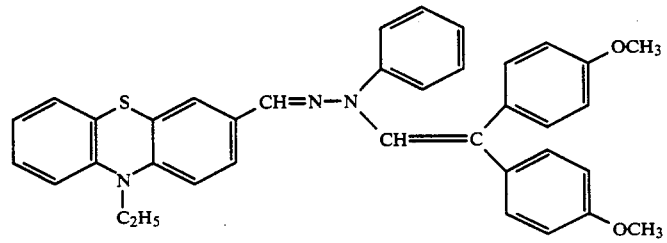
II-(10)
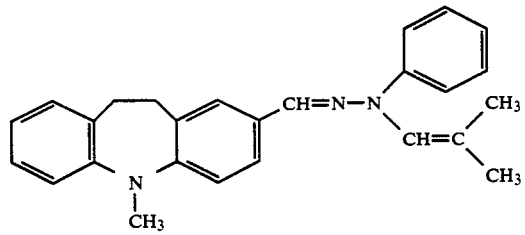
II-(11)
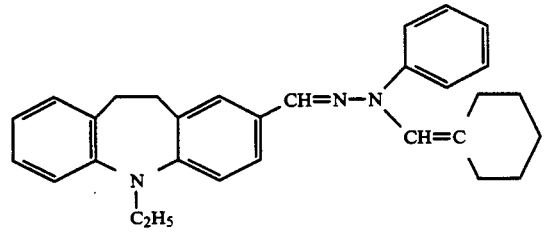
II-(12)
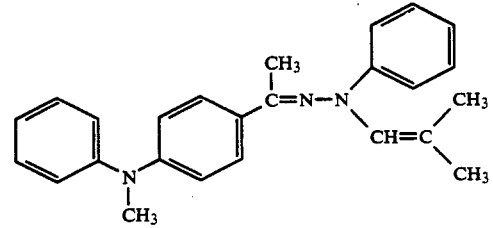
II-(13)

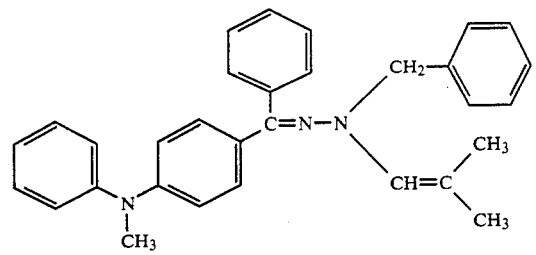
II-(14)
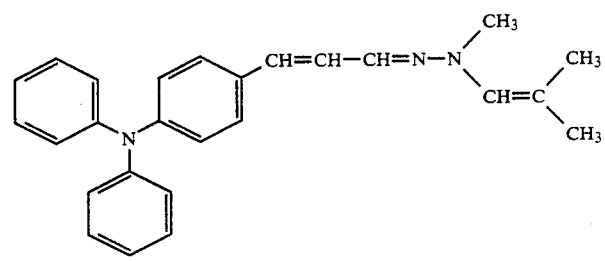
II-(15)
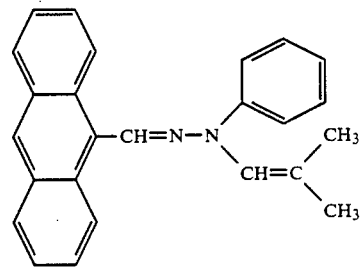
II-(16)
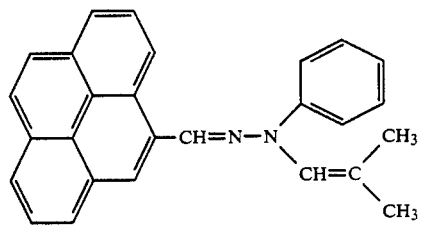
II-(17)
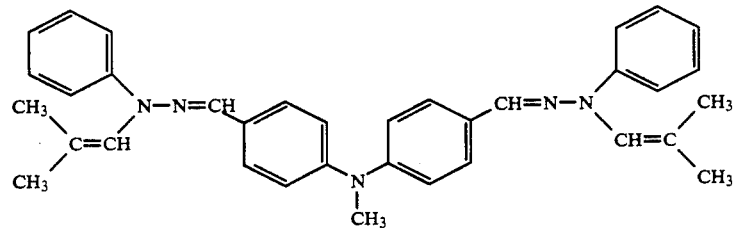
II-(18)
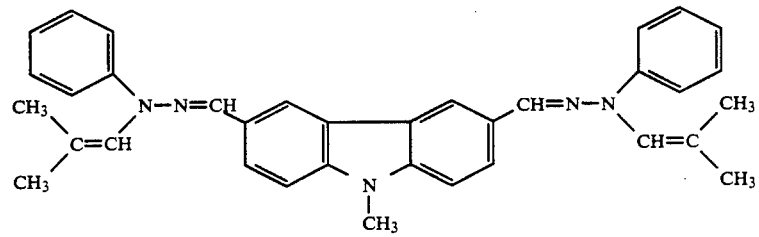
II-(19)

-continued
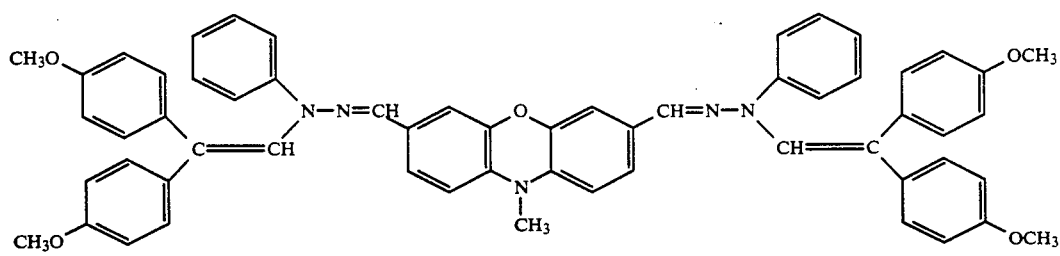
II-(20)
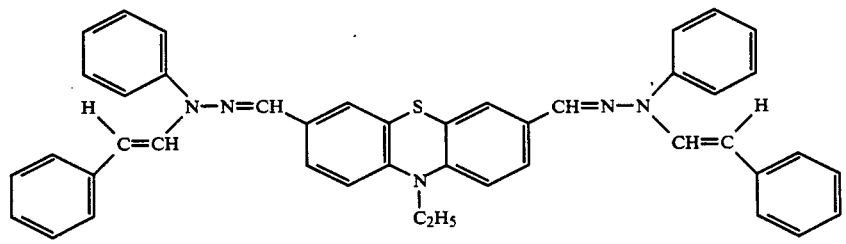
II-(21)
Compounds represented by the formula [III]:
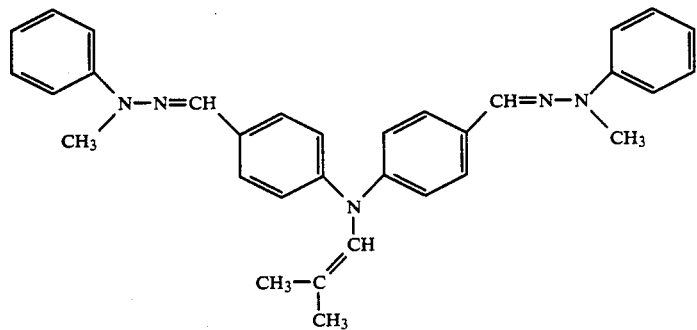
III-(1)
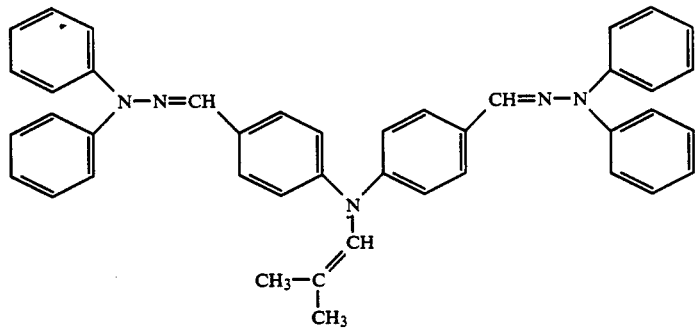
III-(2)
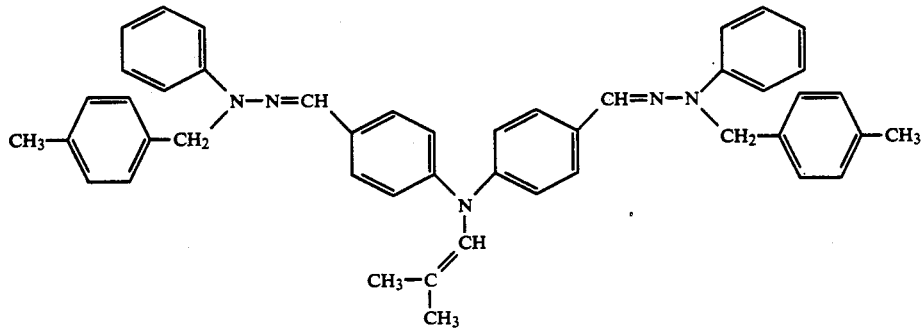
III-(3)

-continued
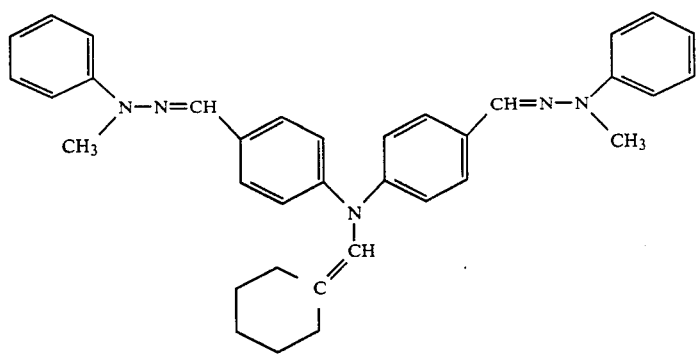
III-(4)
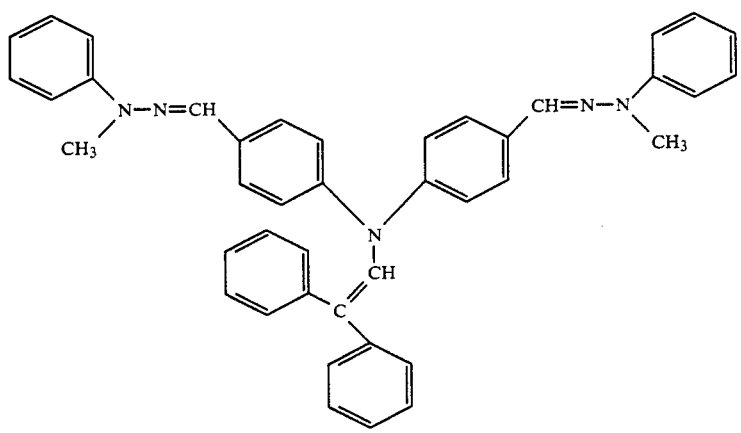
III-(5)
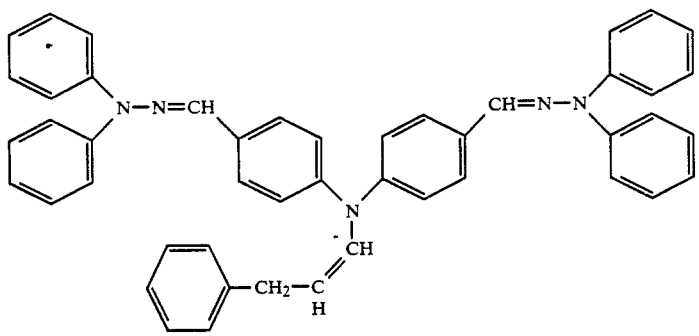
III-(6)
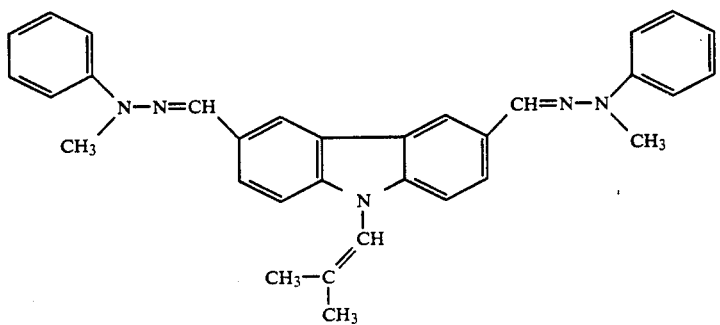
III-(7)

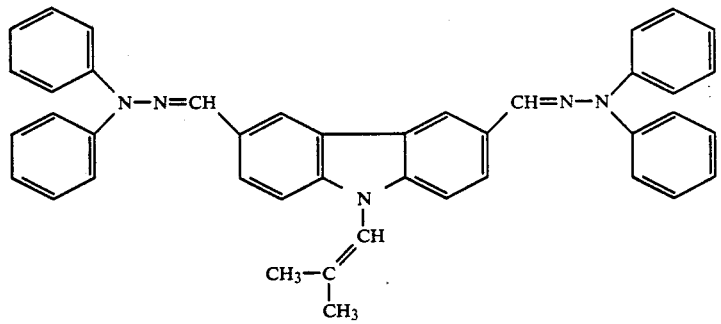
III-(8)
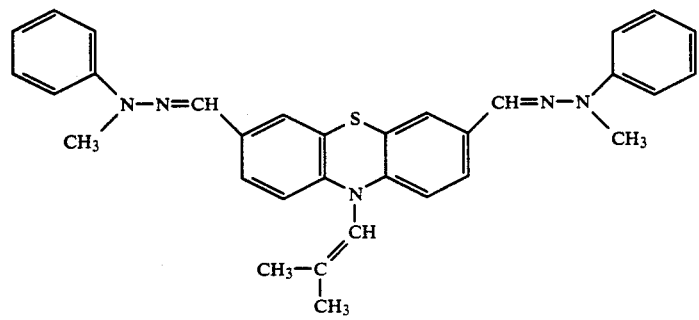
III-(9)
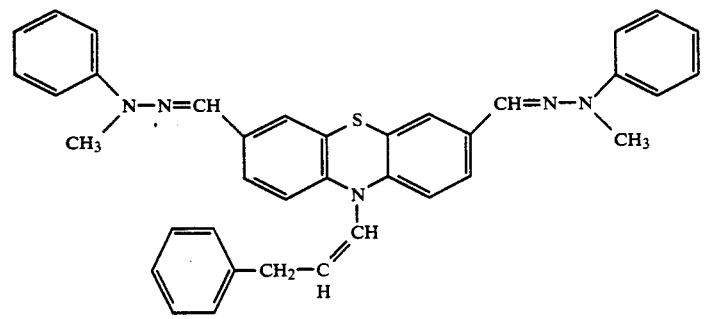
III-(10)
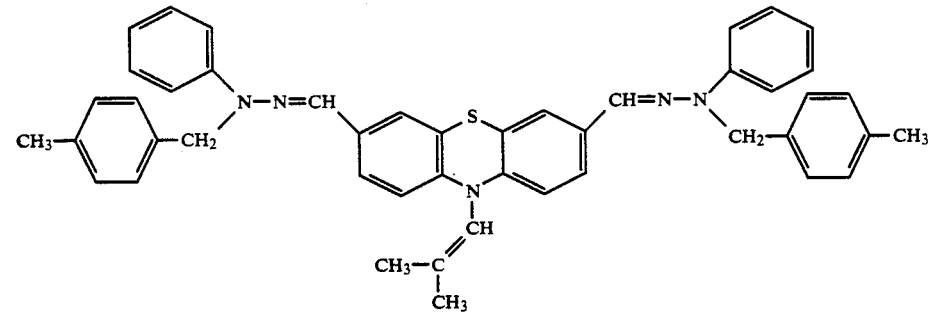
III-(11)
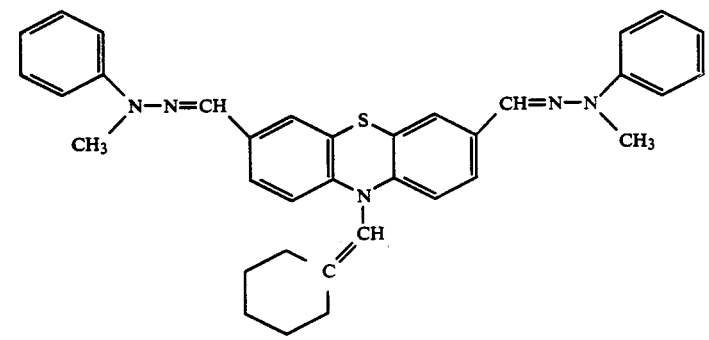
III-(12)

-continued
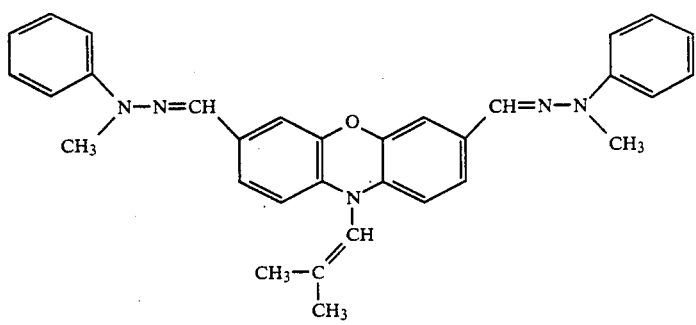
III-(13)
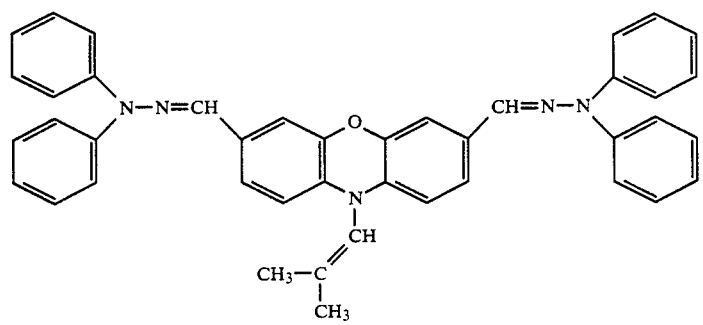
III-(14)
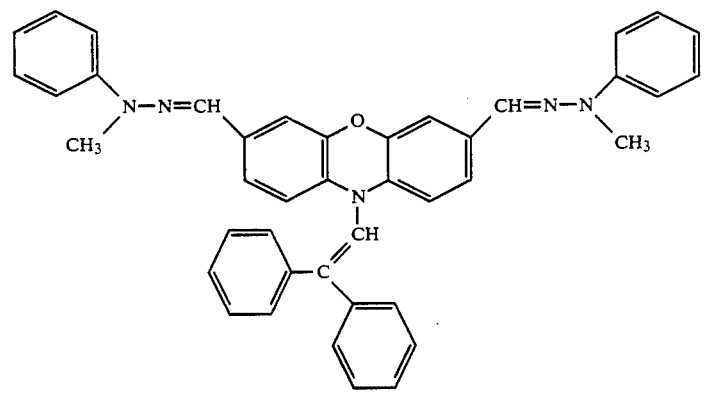
III-(15)
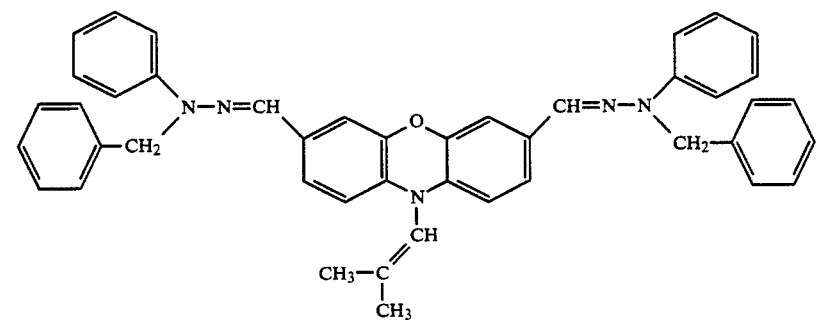
III-(16)

-continued
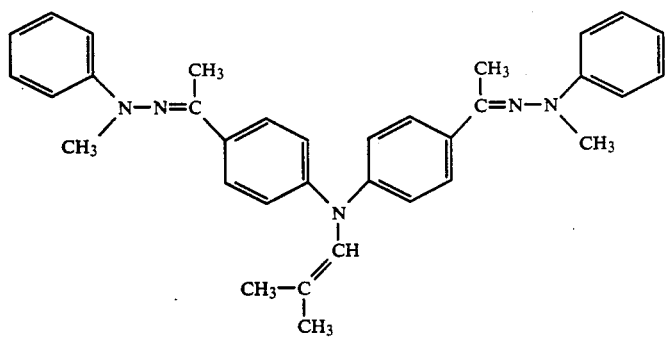
III-(17)
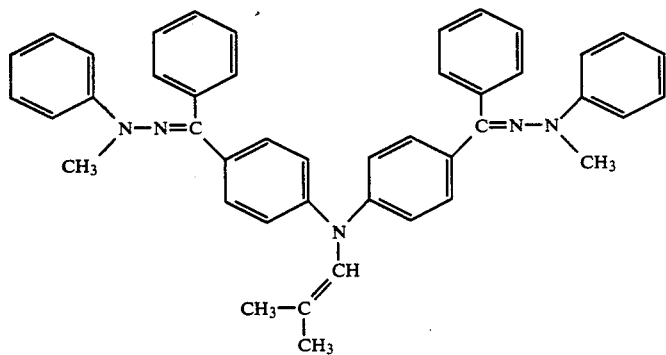
III-(18)
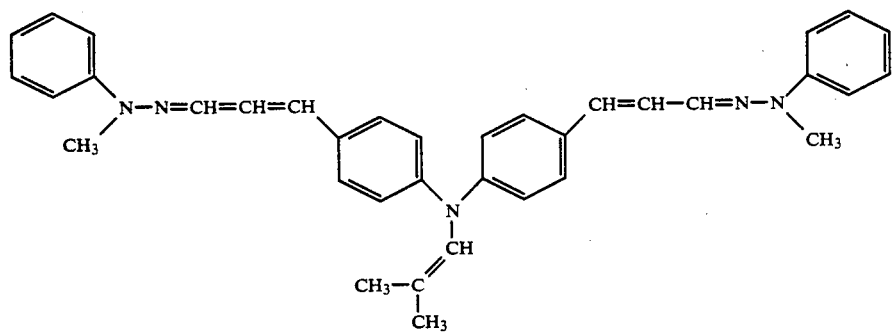
III-(19)
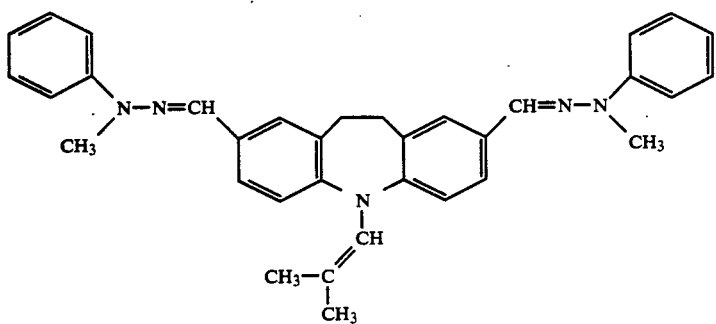
III-(20)

-continued

III-(21)

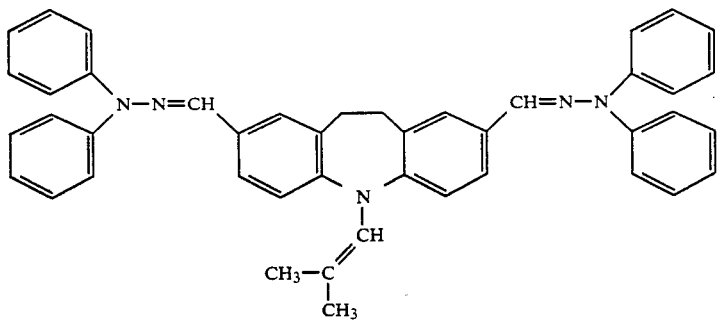

The hydroazone compounds represented by the formulas [I], [II] and [III] can be prepared by the processes as shown in the following synthesis examples.

Synthesis Examples 1 [Compound I-(4)]

2.5 grams of N-β-methallyldiphenylamine-4-carboxaldehyde and 1.3 g of 1-methyl-1-phenylhydrazine were dissolved in 15 ml of DMF and thereto was added 2.2 g of potassium-t-butoxide at room temperature with stirring. After stirring for 2 hours, the reaction mixture was poured into water, neutralized and then extracted with ethyl acetate. The ethyl acetate was distilled off and residue oil was separated and purified by column chromatography to obtain 1.4 g of a light yellow solid. m.p. 100°-104° C.

This compound can also be prepared by the following process. That is, 1.8 g of a hydrazone compound (m.p. 91°-93° C.) obtained from N-β-methallyldiphenylamine-4-carboxaldehyde and 1-phenyl-1-methylhydrazine was dissolved in 5 ml of DMF and thereto was added 1 g of potassium-t-butoxide, followed by stirring for 2 hours at room temperature. Thereafter, the same treatments as above were conducted and the resulting product was recrystallized from acetonitrile to obtain the desired product. Yield: 1.2 g. This product showed depression of melting point when mixed with the starting hydrazone.

Structure of this compound was confirmed by NMR method.

Infrared absorption spectrum of this compound is shown in FIG. 1.

Synthesis Example 2 [Compound I-(20)]

1.45 Gram of hydrazone compound represented by the following formula [IV], 1.23 g of 2,2-bis(p-methoxyphenyl)acetaldehyde and 30 mg of p-toluenesulfonic acid monohydrate were refluxed under heating for 30 hours together with 30 ml of toluene. The product was purified by silica gel chromatography (benzene: hexane=1:1) to obtain 1.2 g of compound I-(20). m.p. 197°-199° C.

HNMR (δ, ppm, CDCl₃)
3.64 (S, 3H), 3.77 (S, 3H) 6.5-7.5 (m, 29H)

[IV]

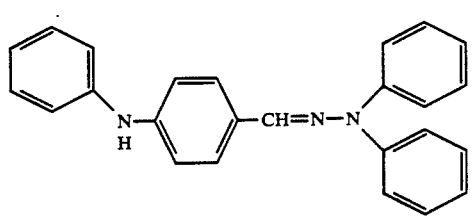

Synthesis Example 3 [Compound I-(55)]

1.60 Gram of hydrazone compound represented by the following formula [V] (which can be prepared by conventional process from N-methallyltetrahydroquinoline) was dissolved in 5 ml of DMF and thereto was added 0.67 g of potassium-t-butoxide at room temperature. After 45 minutes, the reaction mixture was poured into water and extracted with ethyl acetate. Solvent was distilled off and the crude product was recrystallized from acetonitrile to obtain 1.15 g of compound I-(55). m.p. 108.5°-109.5° C.

NMR (δ, ppm, DMSO) 1.64 (S, 3H), 1.78 (S, 3H), 1.93 (m, 2H), 2.80 (t, J=6Hz, 2H), 3.32 (m, 2H), 3.37 (S, 3H), 5.82 (S, 1H), 6.50 (d, J=8.7Hz, 1H), 6.84 (m, 1H), 7.2-7.4 (m, 6H), 7.59 (S, 1H)

[V]

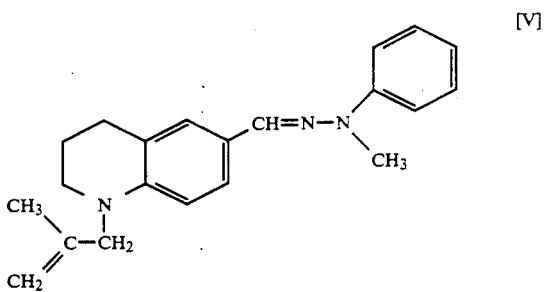

Synthesis Example 4 [Compound I-(87)]

This compound can be prepared through the following steps.

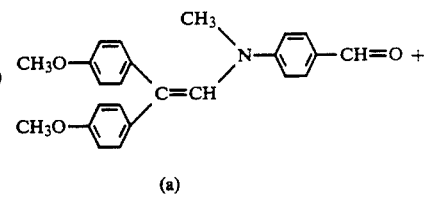

(a)

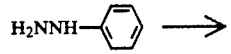

(b)

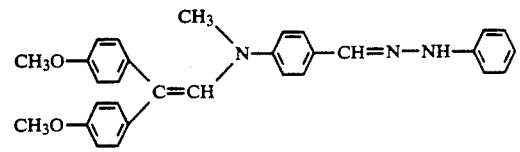

(c)

Compound (C) + OHC—CH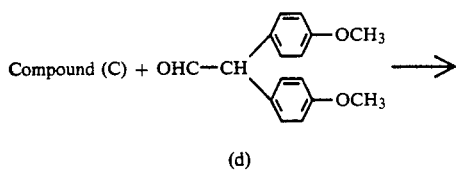 →

(d)

Compound (I-(87))

Preparation of compound (c) in the above steps.

0.747 Gram of the starting compound (a) and 0.238 g of phenylhydrazine were refluxed in 5 ml of ethyl alcohol for 1 hour. The precipitated crystal was collected by filtration and washed with ethyl alcohol to obtain 0.700 g of yellow compound (c) of m.p. 153.0°-158.0° C.

NMR (δ, ppm, DMSO-$d_6$)

2.82 (S, 3H), 3.78 (S, 6H), 6.56 (S, 1H), 6.71 m, 1H), 6.8-7.2 (m, 14H), 7.54 (d, J=8.7Hz, H), 7.82 (S, 1H), 10.6 (S, 1H),

Preparation of compound I-(87) from the compound (c) obtained above.

0.695 g of compound (c) and 0.423 g of 2,2-bis(4-methoxyphenyl)acetaldehyde (compound (d) were refluxed in 25 ml of benzene for 3 hours together with 10 mg of p-toluenesulfonic acid monohydrate. After completion of reaction, benzene was distilled off and the crude product was purified by silica gel column (hexane:ethyl acetate =3:1) to obtain 0.770 g of yellow crystal of compound I-(87) of m.p. 91.0°-95.0° C.

NMR (δ, ppm, DMSO-$d_6$) 2.81 (S, 3H), 3.66 (S, 3H), 3.78 (S, 6H), 3.82 (S, 3H), 6.39 (S, 1H), 6.56 (S, 1H), 6.7-7.2 (m, Zl), 7.36 (d, J=8.7Hz, 2H), 7.60 (d, J=8.7Hz, 2H), 7.95 (S, 1H), Synthesis Example 5 [Compound II-(3)]

1.56 Gram of hydrazone compound shown by the following formula (VI) and 0.50 g of methallyl chloride were dissolved in 10 ml of DMF and thereto was added 1.12·g of potassium-t-butoxide at room temperature. After 4 hours, the reaction mixture was poured into water and precipitate was collected by filtration and recrystallized from acetonitrile to obtain 1.1 g of compound II-(3). m.p. 127.0°-128.0° C.

NMR (δ, ppm, DMSO) 1.36 (t, J=7Hz, 3H), 1.55 (S, 3H), 2.03 (S, 3H), 4.49 (q, J=7Hz, 2H), 5.90 (S, 1H), 6.90 (m, 1H), 7.2-7.4 (m, 5H), .7.50 (t, J=7Hz, 1H), 7.6-7.7 (m, 2H), 7.91 (S, 1H), 7.97 (d, J=7Hz, 1H), 8.24 (d, J=7Hz, 1H), 8.47 (S, 1H).

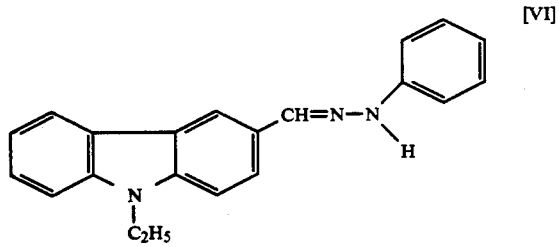

[VI]

Synthesis Example 6 [Compound III-(1)]

1.26 Gram of hydrazone compound represented by the following formula (VII) was dissolved in 40 ml of DMSO and thereto was added 0.58 g of potassium-t-butoxide at room temperature. After 1 hour, 80 ml of methanol was added and precipitate was collected by filtration and recrystallized from ethyl acetate. m.p. 185.4°-186.0° C.

NMR (δ, ppm, CDCl$_3$) 1.38 (S, 3H), 1.79 (S, 3H), 3.38 (S, 6H), 5.91 (S, H), 7.10 (d, J=7.5Hz, 4H), 7.2-7.4 (m, 10H), 7.47 [S, 2H], 7.58 (d, J=7.5Hz, 4H),

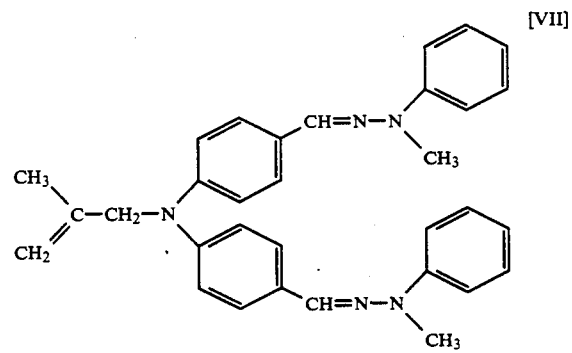

[VII]

The electrophotographic photoreceptor of the present invention is obtained by containing one or more of the hydrazone compounds as shown above and it has excellent properties.

Various methods have been known for use of these hydrazone compounds as electrophotographic photoreceptor.

For example, there are a photoreceptor which comprises a conductive support on which is coated a solution or dispersion of the hydrazone compound and a sensitizing dye in a binder resin, if necessary, with addition of a chemical sensitizer or an electron attractive compound; a photoreceptor in the form of a double layer structure comprising a carrier generation layer and a carrier transport layer wherein a carrier generation layer mainly composed of a carrier generation substance of high carrier generation efficiency such as dye or pigment is provided on a conductive support and thereon is provided a carrier transport layer comprising a solution or a dispersion of the hydrazone compound in a binder resin, if necessary, with addition of a chemical sensitizer or an electron attractive compound; and such photoreceptor as mentioned above wherein the carrier generation layer and the carrier transport layer are provided in the reverse order. The hydrazone compound of the present invention can be applied to all of these photoreceptors.

Support used for preparation of the photo receptor using the compound according to the present invention includes, for example, metallic drum, metal sheet, and sheet-like, drum-like or belt-like paper or plastic film subjected to electroconductive treatment.

As film-forming binder resins used for formation of photosensitive layer on the support, mention may be made of various resins depending on fields in which the photoreceptor is utilized. For example, in case of photoreceptors for use in copying, mention may be made of polystyrene resin, polyvinylacetal resin, polysulfone resin, polycarbonate resin, vinyl acetate/crotonic acid copolymer resin, polyphenylene oxide resin, polyester resin, alkyd resin, polyarylate resin, acrylic resin, methacrylic resin, and phenoxy resin. Among them, polystyrene resin, polyvinylacetal resin, polycarbonate resin, polyester resin, polyarylate resin, and phenol resin are superior in potential characteristics as photoreceptor.

These resins may be used singly or in combination as homopolymers or copolymers.

Amount of these binder resins to be added to photoconductive compound is 0.2-10, preferably 0.5-5 times the weight of the photoconductive compound. If the amount is less than this range, the photoconductive compound is precipitated in or on the photosensitive layer to cause deterioration of adhesion to the support and if it is more than the range, sensitivity is reduced.

Further, some of the film-forming binder resins are rigid and low in mechanical strengths such as tensile strength, flexural strength and compression strength and in order to improve theses properties, plasticity imparting materials can be added.

These materials include, for example, phthalate ester (such as DOP, DBP and DIDP), phosphate ester (such as TCP and TOP), sebacate ester, adipate ester, nitrile rubber, and chlorinated hydrocarbons. If these materials which impart plasticity are added in an amount more than needed, potential characteristics are deteriorated and so they are added preferably in an amount of 20% by weight or less of binder resin.

The sensitizing dyes added to the photosensitive layer include triphenylmethane dyes represented by Methyl Violet, Crystal Violet, Ethyl Violet, Night Blue, and Victoria Blue, xanthene dyes represented by erythrosine, Rhodamine B, Rhodamine 3B, and Acridine Red B, acridine dyes represented by Acridine Orange 2G, Acridine Orange R and Flaveosine, thiazine dyes represented by Methylene Blue and Methylene Green, oxazine dyes represented by Capri Blue and Meldola's Blue, and other cyanine dyes, styryl dyes, pyrylium salts, thiapyrylium salts and squarylium salt dyes.

As photoconductive pigments which generate carrier at very high efficiency upon absorption of light in photosensitive layer, mention may be made of phthalocyanine pigments such as metal-free phthalocyanine and phthalocyanine containing various metals or metal compounds, perylene pigments such as peryleneimide and perylenic acid anhydride, and guinacridone pigments, anthraquinone pigments, and azo pigments.

Among these pigments, bisazo pigments, trisazo pigments and phthalocyanine pigments high in carrier generating efficiency afford high sensitivity and thus provide excellent electrophotographic photoreceptor.

The dye added to photosensitive layer can be used singly as a carrier generation substance, but joint use of this dye with pigment can generate carrier at higher efficiency. Furthermore, inorganic photoconductive substances include selenium, selenium-tellurium alloy, cadmium sulfide, zinc sulfide and amorphous silicon.

In addition to the above-mentioned sensitizers (so-called spectral sensitizers), there may be added sensitizers for further increase of sensitivity (so-called chemical sensitizers).

Such sensitizers include, for example, p-chlorophenol, m-chlorophenol, p-nitrophenol, 4-chloro-m-cresol, p-chlorobenzoylacetanilide, N,N'-diethyl-barbituric acid, 3-(β-oxyethyl)-2-phenyliminothiazolidone, malonic acid dianilide, 3,5,3', 5'-tetrachloromalonic acid dianilide, α-naphthol, and p-nitrobenzoic acid.

Furthermore, it is also possible to add some electron attractive compounds as sensitizers which form a carrier transport complex with the hydrazone compound of the present invention to further enhance the sensitizing effect.

As the electron attractive substances, mention may be made of, for example, 1-chloroanthraquinone, 1-nitroanthraquinone, 2,3 dichloronaphthoquinone, 3,3-dinitrobenzophenone, 4-nitrobenzalmalononitrile, phthalic anhydride, 3-(α-cyano-p-nitrobenzal)phthalide, 2,4,7-trinitrofluorenone, 1-methyl-4-nitrofluorenone, and 2,7 dinitro-3,6-dimethylfluorenone.

If necessary, antioxidant, curl inhibitor, etc. may also be added to the photoreceptor.

The hydrazone compound of the present invention is dissolved or dispersed in a suitable solvent together with the above-mentioned additives depending on the form of photoreceptor, the resulting coating liquid is coated on an electroconductive support mentioned above and is dried to obtain a photoreceptor.

As the coating solvent, for example, halogenated hydrocarbons such as chloroform, dichloroethane, trichloroethane, and trichloroethylene, aromatic hydrocarbons such as benzene, toluene, xylene, and monochlorobenzene, dioxane, tetrahydrofuran, methyl cellosolve, dimethyl cellosolve and methyl cellosolve acetate are used singly or as mixed solvent of two or more of them. If necessary, solvents such as alcohols, acetonitrile, N,N-dimethylformamide, and methyl ethyl ketone may further be added to the above solvents The following nonlimiting examples further explain the present invention.

EXAMPLE 1

A solution prepared by dissolving a pigment represented by the following formula in n-butylamine at a concentration of 1% by weight was coated on a polyester film on which aluminum was vapor deposited as a support and was dried to form a film of carrier generation material of about 0.2 μ thick.

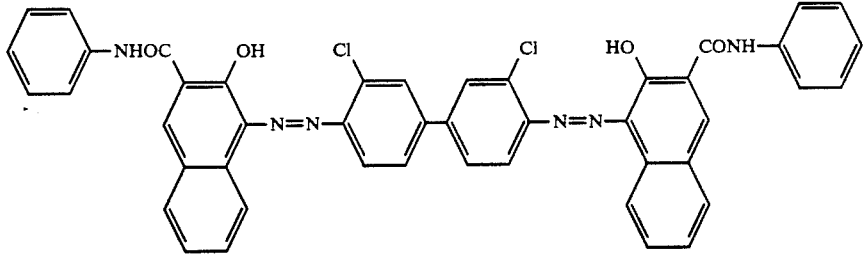

Then, the hydrazone compound of compound No.I-(4) exemplified hereinbefore was mixed with a polyarylate resin(U-POLYMER manufactured by Unitika Ltd.) at a weight ratio of 1:1 and the mixture was dissolved in dichloroethane as a solvent to prepare a 10% solution. This solution was coated on the film of carrier generation material formed hereabove by an applicator to form a carrier transport layer having a dry thickness of 20 μ.

Electrophotographic characteristics of the resulting electrophotographic photoreceptor were evaluated by an electrostatic recording paper testing apparatus (SP- 428 manufactured by Kawaguchi Denki Seisakusho Co.).

Measuring conditions: Applied voltage $-6$ KV, Static No. 3.

As a result, half decay exposure with white light was 2.1 lux.sec which means very high sensitivity. In addition, evaluation for repeated use was conducted using this apparatus. As a result of repeated uses of 1000 times, initial potential at the first time was $-970$ V and that at 1000th time was $-950$ V. Thus, it can be seen that reduction of potential due to repeated use was small and potential was stable.

EXAMPLES 2-5

Photoreceptors were prepared in the same manner as in Example 1 except that hydrazone compounds shown in Table 1 were used in place of the hydrazone compound used in Example 1. Half decay exposure $E_{\frac{1}{2}}$ (lux.-sec) and initial potential $V_0$ (volt) of the resulting photoreceptors were measured under the same measuring conditions as in Example 1 and the results are shown in Table 1. Further, the photoreceptors were subjected to repeated test cycles of 1000 times, one test cycle consisting of charging and removing of potential (removal of potential was carried out by exposing to white light of 400 lux for 1 second) and initial potential $V_0$ (volt) and half decay exposure $E_{\frac{1}{2}}$ are shown in Table 1.

TABLE 1

| Ex- ample | Hydrazone compound | The 1st cycle | | The 1000th cycle | |
|---|---|---|---|---|---|
| | | $V_0$ (volt) | $E_{\frac{1}{2}}$ (lux · sec) | $V_0$ (volt) | $E_{\frac{1}{2}}$ (lux · sec) |
| 2 | I-(3) | $-1020$ | 2.5 | $-990$ | 2.4 |
| 3 | I-(6) | $-1050$ | 3.1 | $-1010$ | 2.9 |
| 4 | I-(11) | $-910$ | 2.8 | $-900$ | 2.8 |
| 5 | I-(15) | $-870$ | 3.4 | $-850$ | 3.4 |

EXAMPLES 6-9

A bisazo pigment having the following formula was used as carrier generation substance.

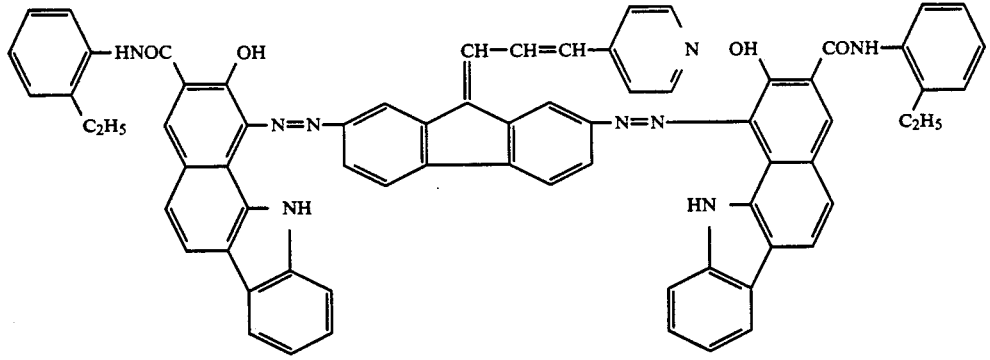

That is, 1 part by weight of this pigment and 1 part by weight of a polyester resin (BYRON 200 manufactured by Toyobo Co., Ltd.) were mixed with 100 parts by weight of tetrahydrofuran and the mixture was dispersed by a paint conditioner apparatus together with glass beads for 2 hours. The resulting pigment dispersion was coated on the same support as used in Example 1 by an applicator to form a carrier generation layer Thickness of this thin film was about 0.2 µ.

Then, a carrier transport layer was formed in the same manner as in Example 1 using compounds I-(3), I-(4), I-(13) and I=(14) to obtain photoreceptors. These photoreceptors were evaluated under the same measuring conditions as in Example 1. The results are shown in Table 2.

TABLE 2

| Example | Hydrazone compound | The 1st cycle | | The 1000th cycle | |
|---|---|---|---|---|---|
| | | $V_0$ (volt) | $E_{\frac{1}{2}}$ (lux · sec) | $V_0$ (volt) | $E_{\frac{1}{2}}$ (lux · sec) |
| 6 | I-(3) | $-800$ | 1.5 | $-800$ | 1.5 |
| 7 | I-(4) | $-760$ | 1.4 | $-750$ | 1.3 |
| 8 | I-(13) | $-820$ | 1.9 | $-790$ | 1.7 |
| 9 | I-(14) | $-840$ | 1.7 | $-810$ | 1.8 |

EXAMPLE 10

Styrene/n-butyl methacrylate/methacrylic acid copolymer (acid value 185) and compound I-(3) were mixed at a weight ratio of 1.5:1 and thereto was added ε-copper phthalocyanine in an amount of 10% by weight of the hydrazone compound and the mixture was dispersed in a ball mill with addition of dioxane solvent so that total solid content was 30% by weight. This dispersion was coated on an aluminum sheet which had been sandblasted and surface oxidized by a wire bar and dried to obtain a photoreceptor for printing plate which had a film thickness of about 4 µ.

This photoreceptor was evaluated on the electrophotogarphic characteristics by the above electrostatic recording paper testing apparatus. Measurement was conducted under the evaluation conditions: Applied voltage $-5.5$ KV, Static No. 3 to obtain an initial potential of $-430$ volts and a half decay exposure of 6.3 lux.sec.

This photoreceptor was subjected to toner development treatment and then to etching treatment with an alkali processing solution(for example, an aqueous solution containing 3% of triethanolamine, 10% of ammonium carbonate and 20% of polyethylene glycol having a mean molecular weight of 190-210). Non-image portions were easily dissolved out and toner images remained Then, the surface of this plate was treated with water containing sodium silicate to obtain a strong printing plate.

It was found that printing endurance of this printing plate in offset printing was more than 50,000 prints.

EXAMPLE 11

One part by weight of a pigment represented by the following formula and 1 part by weight of a polyester resin (BYRON 200 manufactured by Toyobo Co., Ltd.) were mixed with 100 parts by weight of tetrahydrofuran and the mixture was dispersed together with glass beads for 2 hours by a paint conditioner apparatus.

exposing to white light of 400 lux for 1 second) and initial potential $V_0$ (volt) and half decay exposure $E_{\frac{1}{2}}$ are shown in Table 3.

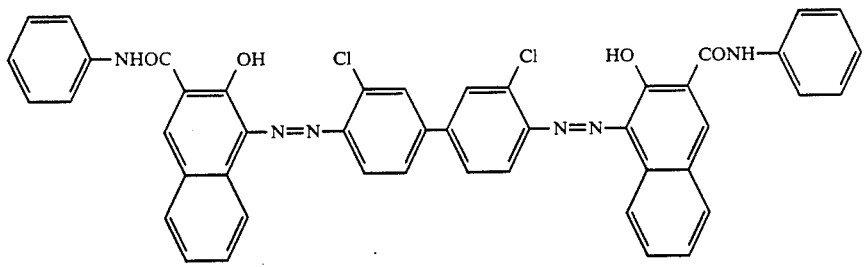

The resulting pigment dispersion was coated on a polyester film on which aluminum had been vapor deposited by an applicator to form a film of carrier generation substance of about 0.2 µ thick.

Then, hydrazone compound I-(21) and a polyarylate resin (U-POLYMER manufactured by Unitika Ltd.) were mixed at a weight ratio of 1:1 and 10% solution of this mixture in dichloroethane as a solvent was prepared. This solution was coated on the film of the carrier generation substance by an applicator to form a carrier transport layer of 20 µ in dry thickness.

Thus obtained electrophotographic photoreceptor was evaluated on its electrophotographic characteristics by the same electrostatic recording paper testing apparatus as used in Example 1 under the measuring conditions of applied voltage −6 KV, static No. 3.

The half decay exposure with white light was 2.2 lux.sec which indicates very high sensitivity.

Evaluation for repeated use was conducted using the above apparatus. Change in potential by repeated use of 1000 times was examined to obtain initial potential of −980 V for the first time and initial potential at 1000th time of −950 V. It can be seen that reduction of potential due to repeated use was small and potential was stable. Thus, excellent characteristics were exhibited.

EXAMPLES 12-15

Photoreceptors were prepared in the same manner as in Example 11 except that hydrazone compounds shown in Table 3 were used in place of the compound used in Example 11. Half decay exposure $E_{\frac{1}{2}}$ (lux.sec) and initial potential $V_0$ (volt) were measured under the same measuring conditions as in Example 11 and the results are shown in Table 3. Furthermore, the photoreceptors were subjected to 1000 test cycles, each cycle comprising charging and removing of potential (by

TABLE 3

| Example | Hydrazone compound | The 1st cycle | | The 1000th cycle | |
|---|---|---|---|---|---|
| | | $V_0$ (volt) | $E_{\frac{1}{2}}$ (lux · sec) | $V_0$ (volt) | $E_{\frac{1}{2}}$ (lux · sec) |
| 12 | I-(20) | −1010 | 2.6 | −980 | 2.6 |
| 13 | I-(22) | −1070 | 2.9 | −1040 | 2.8 |
| 14 | I-(28) | −920 | 3.1 | −900 | 3.0 |
| 15 | I-(31) | −910 | 2.8 | −900 | 2.8 |

EXAMPLES 16-19

A bisazo pigment having the following formula was used as charge generation substance.

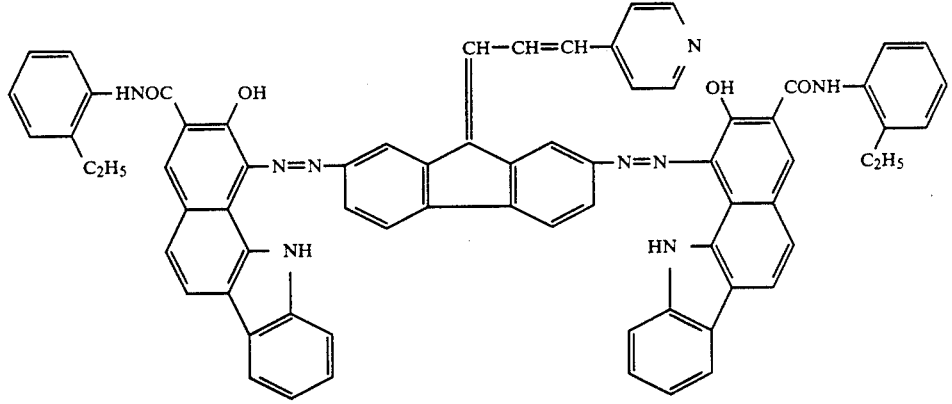

That is, 1 part by weight of this pigment and 1 part by weight of a polyester resin (BYRON 200) were mixed with 100 parts by weight of tetrahydrofuran and the mixture was dispersed together with glass beads for 2 hours by a paint conditioner apparatus. The resulting pigment dispersion was coated on the same support as used in Example 11 by an applicator to form a carrier generation layer. Thickness of this layer was about 0.2 µ.

Thereafter, carrier transport layer was formed thereon using compounds I-(20), I-(21), I-(30) and I-(31) in the same manner as in Example 11 to make photoreceptors. The resulting photoreceptors were evaluated in the same manner as in Example 11. The results are shown in Table 4.

TABLE 4

| Example | Hydrazone compound | The 1st cycle | | The 1000th cycle | |
|---|---|---|---|---|---|
| | | $V_0$ (volt) | $E_{\frac{1}{2}}$ (lux · sec) | $V_0$ (volt) | $E_{\frac{1}{2}}$ (lux · sec) |
| 16 | I-(20) | −780 | 1.5 | −770 | 1.5 |

TABLE 4-continued

| Example | Hydrazone compound | The 1st cycle | | The 1000th cycle | |
|---|---|---|---|---|---|
| | | $V_0$ (volt) | $E_{\frac{1}{2}}$ (lux · sec) | $V_0$ (volt) | $E_{\frac{1}{2}}$ (lux · sec) |
| 17 | I-(21) | −800 | 1.6 | −770 | 1.5 |
| 18 | I-(30) | −850 | 1.8 | −830 | 1.7 |
| 19 | I-(31) | −910 | 1.7 | −900 | 1.7 |

EXAMPLE 20

One part by weight of a pigment represented by the following formula and 1 part by weight of a polyester resin (BYRON 200) were mixed with 100 parts by weight of tetrahydrofuran and the mixture was dispersed together with glass beads for 2 hours by a paint conditioner apparatus.

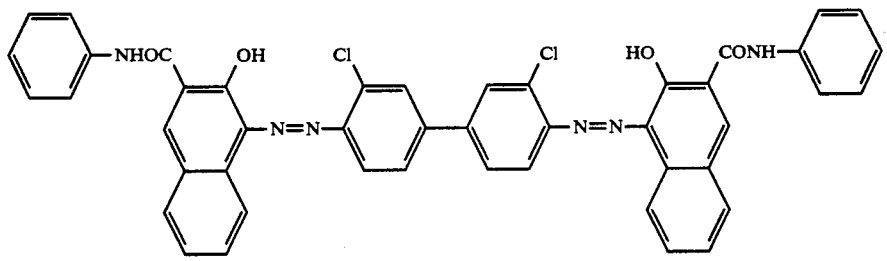

The resulting pigment dispersion was coated on an aluminum-vapor deposited polyester film by an applicator and dried to form a film of carrier generation substance of about 0.2 μ thick.

Then, hydrazone compound represented by I-(35) was mixed with a polyarylate resin (U-POLYMER manufactured by Unitika Ltd.) at a weight ratio of 1:1 and a 10% solution of the mixture in dichloroethane was prepared. This solution was coated on the film of carrier generation substance formed hereabove by an applicator to form a carrier transport layer of 20 μ in dry thickness.

The resulting laminate photoreceptor was evaluated in the same manner as in Example 11. Half decay exposure with white light was 2.2 lux.sec which means a very high sensitivity.

Furthermore, evaluation for repeated use was conducted using the same apparatus as in Example 11. Change in potential due to repeated use of 1000 times was examined. Initial potential at the first time was −890 V and initial potential at 1000th time was −870 V. It can be seen that reduction in potential due to repeated use was small and the potential was stable. Thus, excellent characteristics were exhibited.

EXAMPLES 21-24

Photoreceptors were prepared in the same manner as in Example 20 except that hydrazone compounds shown in Table 5 were used in place of the hydrazone compound used in Example 20 and half decay exposure $E_{\frac{1}{2}}$ (lux.sec) and initial potential $V_0$ (volt) were measured under the same measuring conditions as in Example 20. The results are shown in Table 5. Furthermore, these photoreceptors were subjected to 1000 test cycles, each cycle consisting of charging and removing of potential (removal of potential was effected by exposing to white light of 400 lux for 1 second). Initial potential $V_0$ (volt) and half decay exposure are shown in Table 5.

TABLE 5

| Example | Hydrazone compound | The 1st cycle | | The 1000th cycle | |
|---|---|---|---|---|---|
| | | $V_0$ (volt) | $E_{\frac{1}{2}}$ (lux · sec) | $V_0$ (volt) | $E_{\frac{1}{2}}$ (lux · sec) |
| 21 | I-(36) | −940 | 2.7 | −920 | 2.7 |
| 22 | I-(41) | −900 | 2.9 | −880 | 2.8 |
| 23 | I-(44) | −910 | 3.1 | −900 | 3.0 |
| 24 | I-(53) | −870 | 2.6 | −850 | 2.6 |

EXAMPLES 25-28

A bisazo pigment of the following formula was used as carrier generation substance.

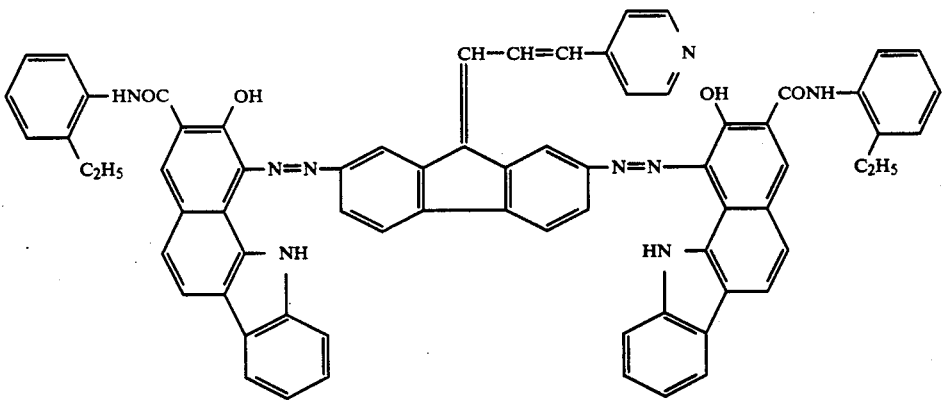

That is, 1 part by weight of this pigment and 1 part by weight of a polyester resin(BYRON 200) were mixed with 100 parts by weight of tetrahydrofuran and the mixture was dispersed together with glass beads for 2 hours by a paint conditioner apparatus. The resulting pigment dispersion was coated on the same support as used in Example 20 by an applicator to form a carrier generation layer of about 0.2 μ thick.

Then, carrier transport layer was formed in the same manner as in Example 20 using compounds shown in Table 6 to make photoreceptors. These photoreceptors were evaluated under the same measuring conditions as in Example 20. The results are shown in Table 6.

TABLE 6

| Example | Hydrazone compound | The 1st cycle | | The 1000th cycle | |
|---|---|---|---|---|---|
| | | $V_0$ (volt) | $E_{\frac{1}{2}}$ (lux · sec) | $V_0$ (volt) | $E_{\frac{1}{2}}$ (lux · sec) |
| 25 | I-(36) | −930 | 1.6 | −910 | 1.6 |
| 26 | I-(38) | −910 | 1.7 | −900 | 1.6 |
| 27 | I-(50) | −870 | 1.9 | −860 | 1.8 |
| 28 | I-(53) | −850 | 1.9 | −820 | 1.9 |

EXAMPLE 29

One part by weight of a pigment represented by the following formula and 1 part by weight of a polyester resin (BYRON 200 manufactured by Toyobo Co., Ltd.) were mixed with 100 parts by weight of tetrahydrofuran and the mixture was dispersed together with glass beads for 2 hours by a paint conditioner apparatus.

apparatus as used in Example 11 under the measuring conditions of applied voltage −6 KV, static No. 3.

The half decay exposure with white light at charging was 2.1 lux.sec which indicates very high sensitivity.

Evaluation for repeated use was conducted using the above apparatus. Change in potential by repeated use of 1000 times was examined to obtain initial potential of −970 V for the first time and initial potential for 1000th time of −940 V. It can be seen that reduction of potential due to repeated use was small and potential was stable. Thus, excellent characteristics were exhibited.

EXAMPLES 30-33

Photoreceptors were prepared in the same manner as in Example 29 except that hydrazone compounds shown in Table 7 were used in place of the compound used in Example 29. Half decay exposure E1/2 (lux.sec) and initial potential $V_0$ (volt) were measured under the same measuring conditions as in Example 29 and the results are shown in Table 7. Furthermore, the photoreceptors were subjected to 1000 test cycles, each cycle comprising charging and removing of potential (removal of potential was effected by exposing to white light of 400 lux for 1 second) and initial potential $V_0$

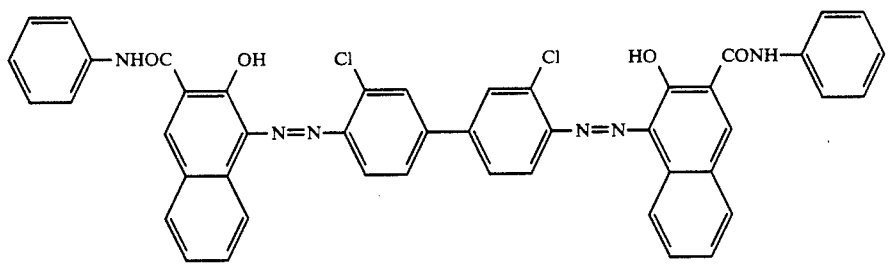

50

The resulting pigment dispersion was coated on a polyester film on which aluminum had been vapor deposited by an applicator to form a film of carrier generation substance of about 0.2 μ thick.

Then, hydrazone compound I-(55) and a polyarylate resin (U-POLYMER manufactured by Unitika Ltd.) were mixed at a weight ratio of 1:1 and 10% solution of this mixture in dichloroethane as a solvent was prepared. This solution was coated on the film of the carrier generation substance by an applicator to form a carrier transport layer of 20 μ in dry thickness.

Thus obtained electrophotographic photo receptor was evaluated on its electrophotographic characteristics by the same electrostatic recording paper testing (volt) and half decay exposure are shown in Table 7.

TABLE 7

| Example | Hydrazone compound | The 1st cycle | | The 1000th cycle | |
|---|---|---|---|---|---|
| | | $V_0$ (volt) | $E_{\frac{1}{2}}$ (lux · sec) | $V_0$ (volt) | $E_{\frac{1}{2}}$ (lux · sec) |
| 30 | I-(56) | −1050 | 2.4 | −980 | 2.4 |
| 31 | I-(57) | −1020 | 2.5 | −1010 | 2.5 |
| 32 | I-(66) | −930 | 3.1 | −900 | 3.0 |
| 33 | I-(67) | −940 | 2.8 | −920 | 2.8 |

EXAMPLES 34-37

A bisazo pigment having the following formula was used as charge generation substance.

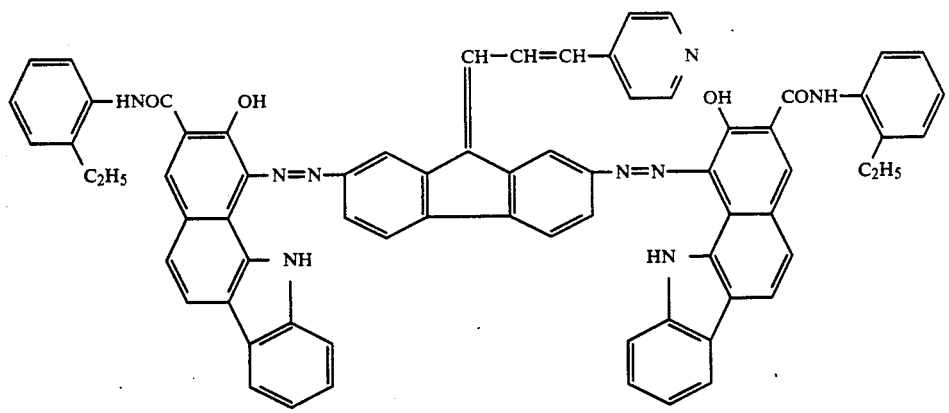

That is, 1 part by weight of this pigment and 1 part by weight of a polyester resin(BYRON 200) were mixed with 100 parts by weight of tetrahydrofuran and the mixture was dispersed together with glass beads for 2 hours by a paint conditioner apparatus. The resulting pigment dispersion was coated on the same support as used in Example 29 by an applicator to form a carrier generation layer. Thickness of this layer was about 0.2 μ.

Thereafter, carrier transport layer was formed thereon using compounds shown in Table 8 in the sam manner as in Example 29 to make photoreceptors. The resulting photoreceptors were evaluated in the same manner as in Example 29. The results are shown in Table 8.

TABLE 8

| Example | Hydrazone compound | The 1st cycle | | The 1000th cycle | |
|---|---|---|---|---|---|
| | | $V_0$ (volt) | $E_{\frac{1}{2}}$ (lux · sec) | $V_0$ (volt) | $E_{\frac{1}{2}}$ (lux · sec) |
| 34 | I-(57) | −810 | 1.6 | −770 | 1.5 |
| 35 | I-(58) | −800 | 1.6 | −770 | 1.5 |
| 36 | I-(66) | −840 | 1.7 | −830 | 1.7 |
| 37 | I-(67) | −810 | 1.7 | −800 | 1.7 |

EXAMPLE 38

One part by weight of a pigment represented by the following formula and 1 part by weight of a polyester resin (BYRON 200) were mixed with 100 parts by weight of tetrahydrofuran and the mixture was dispersed together with glass beads for 2 hours by a paint conditioner apparatus.

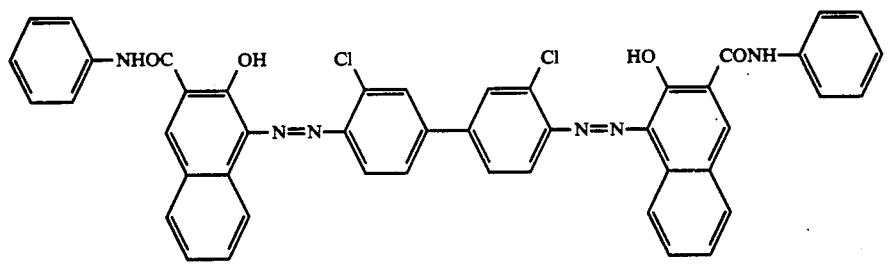

The resulting pigment dispersion was coated on an aluminum-vapor deposited polyester film by an applicator and dried to form a carrier generation layer of about 0.2 μ thick.

Then, hydrazone compound represented by I-(74) was mixed with a polyarylate resin(U-POLYMER manufactured by Unitika Ltd.) at a weight ratio of 1:1 and a 10% solution of the mixture in dichloroethane was prepared. This solution was coated on the carrier generation layer formed here above by an applicator to form a carrier transport layer of 20 μ in dry thickness.

The resulting photoreceptor was evaluated in the same manner as in Example 11. Half decay exposure with white light was 2.9 lux.sec which means a very high sensitivity.

Furthermore, evaluation for repeated use was conducted. Change in potential due to repeated use of 1000 times was examined. Initial potential at the first time was −680 V and initial potential at 1000th time was −640 V. It can be seen that reduction in potential due to repeated use was small and the potential was stable. Thus, excellent characteristics were exhibited.

EXAMPLES 39–43

Photoreceptors were prepared in the same manner as in Example 38 except that hydrazone compounds shown in Table 9 were used in place of the hydrazone compound used in Example 38 and half decay exposure $E_{\frac{1}{2}}$ (lux.sec) and initial potential $V_0$ (volt) were measured under the same measuring conditions as in Example 38. The results are shown in Table 9. Furthermore, these photoreceptors were subjected to 1000 test cycles, each cycle consisting of charging and removing of potential (removal of potential was effected by exposing to white light of 400 lux for 1 second). Initial potential $V_0$ (volt) and half decay exposure are shown in Table 9.

TABLE 9

| Example | Hydrazone compound | The 1st cycle | | The 1000th cycle | |
|---|---|---|---|---|---|
| | | $V_0$ (volt) | $E_{\frac{1}{2}}$ (lux · sec) | $V_0$ (volt) | $E_{\frac{1}{2}}$ (lux · sec) |
| 39 | I-(77) | −710 | 3.0 | −680 | 3.0 |
| 40 | I-(79) | −730 | 2.8 | −690 | 2.6 |

TABLE 9-continued

| Example | Hydrazone compound | The 1st cycle V₀ (volt) | The 1st cycle E½ (lux · sec) | The 1000th cycle V₀ (volt) | The 1000th cycle E½ (lux · sec) |
|---|---|---|---|---|---|
| 41 | I-(83) | −690 | 2.6 | −645 | 2.5 |
| 42 | I-(85) | −670 | 3.1 | −630 | 3.0 |
| 43 | I-(87) | −780 | 3.2 | −770 | 3.0 |

EXAMPLES 44–47

A bisazo pigment of the following formula was used as carrier generation substance.

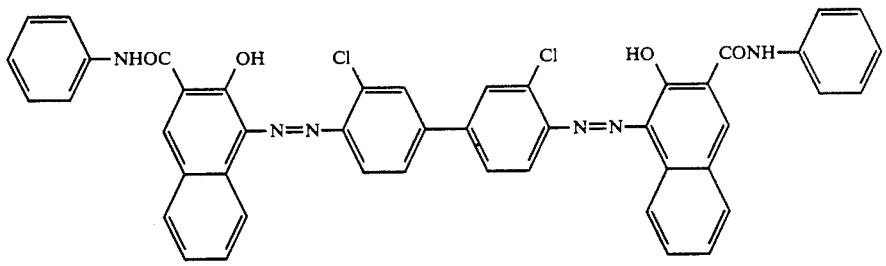

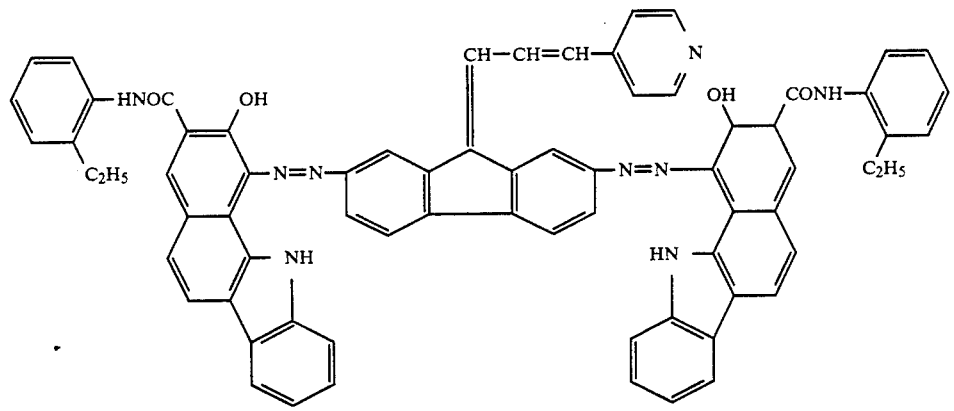

That is, 1 part by weight of this pigment and 1 part by weight of a polyester resin(BYRON 200) were mixed with 100 parts by weight of tetrahydrofuran and the mixture was dispersed together with glass beads for 2 hours by a paint conditioner apparatus. The resulting pigment dispersion was coated on the same support as used in Example 38 by an applicator to form a carrier generation layer of about 0.2 μ thick.

Then, carrier transport layer was formed in the same manner as in Example 38 using compounds shown in Table 10 to make photoreceptors. These photoreceptors were evaluated under the same measuring conditions as in Example 38. The results are shown in Table 10.

TABLE 10

| Example | Hydrazone compound | The 1st cycle V₀ (volt) | The 1st cycle E½ (lux · sec) | The 1000th cycle V₀ (volt) | The 1000th cycle E½ (lux · sec) |
|---|---|---|---|---|---|
| 44 | I-(74) | −790 | 2.5 | −765 | 2.4 |
| 45 | I-(83) | −810 | 2.4 | −770 | 2.2 |
| 46 | I-(86) | −785 | 2.4 | −750 | 2.3 |
| 47 | I-(92) | −760 | 2.7 | −720 | 2.3 |

EXAMPLE 48

One part of weight of a pigment represented by the following formula and 1 part by weight of a polyester resin (BYRON 200 manufactured by Toyobo Co., Ltd.) were mixed with 100 parts by weight of tetrahydrofuran and the mixture was dispersed together with glass beads for 2 hours by a paint conditioner apparatus.

The resulting pigment dispersion was coated on a polyester film on which aluminum had been vapor deposited by an applicator to form a film of carrier generation substance of about 0.2 μ thick.

Then, hydrazone compound II-(1) and a polyarylate resin (U-POLYMER manufactured by Unitika Ltd.) were mixed at a weight ratio of 1:1 and 10% solution of this mixture in dichloroethane as a solvent was prepared. This solution was coated on the film of the carrier generation substance by an applicator to form a carrier transport layer of 20 μ in dry thickness.

Thus obtained electrophotographic photoreceptor was evaluated on its electrophotographic characteristics by the same electrostatic recording paper testing apparatus as used in Example 1 under the measuring conditions of applied voltage −6 KV, static No. 3.

The half decay exposure with white light at charging was 2.3 lux.sec which indicates very high sensitivity.

Evaluation for repeated use was conducted using the above apparatus. Change in potential by repeated use of 1000 times was examined to obtain initial potential of of −950 V for the first time and initial potential at 1000th time of −930 V. It can be seen that reduction of potential due to repeated use was small and potential was stable. Thus, excellent characteristics were exhibited.

EXAMPLES 49–52

Photoreceptors were prepared in the same manner as in Example 48 except that hydrazone compounds shown in Table 11 were used in place of the compound used in Example 48. Half decay exposure E½ (lux.sec) and initial potential V₀ (volt) were measured under the same measuring conditions as in Example 48 and the results are shown in Table 11. Furthermore, the photoreceptors were subjected to 1000 test cycles, each cycle comprising charging and removing of potential (removal of potential was effected by exposing to white light of 400 lux for 1 second) and initial potential V₀ (volt) and half decay exposure E½ are shown in Table 11.

TABLE 11

| Example | Hydrazone compound | The 1st cycle V₀ (volt) | E½ (lux · sec) | The 1000th cycle V₀ (volt) | E½ (lux · sec) |
|---|---|---|---|---|---|
| 49 | II-(2) | −960 | 2.8 | −930 | 2.8 |
| 50 | II-(3) | −930 | 2.6 | −900 | 2.5 |
| 51 | II-(17) | −1010 | 3.0 | −980 | 3.0 |
| 52 | II-(20) | −1030 | 3.2 | −990 | 3.1 | same manner as in Example 48. The results are shown in Table 12.

TABLE 12

| Example | Hydrazone compound | The 1st cycle V₀ (volt) | E½ (lux · sec) | The 1000th cycle V₀ (volt) | E½ (lux · sec) |
|---|---|---|---|---|---|
| 53 | II-(2) | −850 | 1.7 | −850 | 1.7 |
| 54 | II-(4) | −870 | 1.5 | −830 | 1.4 |
| 55 | II-(16) | −810 | 1.8 | −800 | 1.8 |
| 56 | II-(19) | −890 | 1.8 | −820 | 1.6 |

EXAMPLE 57

One part by weight of a pigment represented by the following formula and 1 part by weight of a polyester resin (BYRON 200 manufactured by Toyobo Co., Ltd.) were mixed with 100 parts by weight of tetrahydrofuran and the mixture was dispersed together with glass beads for 2 hours by a paint conditioner apparatus.

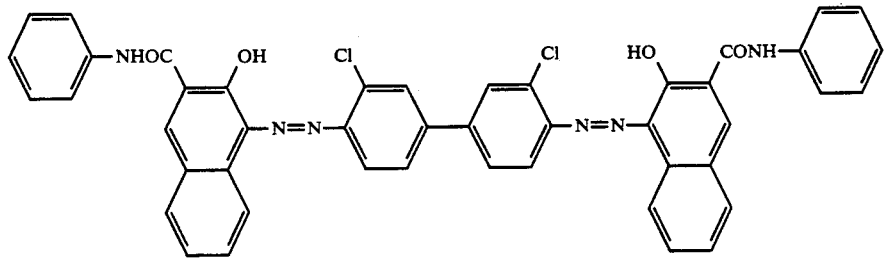

The resulting pigment dispersion was coated on a polyester film on which aluminum had been vapor deposited by an applicator to form a film of carrier generation substance of about 0.2 μ thick.

Then, hydrazone compound III-(1) and a polyarylate

EXAMPLES 53-56

A bisazo pigment having the following formula was used as charge generation substance.

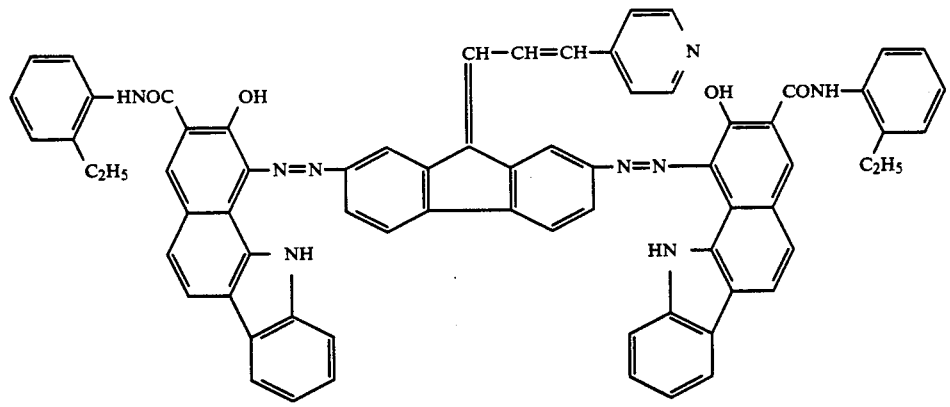

That is, 1 part by weight of this pigment and 1 part by weight of a polyester resin (BYRON 200) were mixed with 100 parts by weight of tetrahydrofuran and the mixture was dispersed together with glass beads for 2 hours by a paint conditioner apparatus. The resulting pigment dispersion was coated on the same support as used in Example 48 by an applicator to form a carrier generation layer. Thickness of this layer was about 0.2 μ.

Thereafter, carrier transport layer was formed thereon using compounds shown in Table 12 in the same manner as in Example 48 to make photoreceptors. The resulting photoreceptors were evaluated in the resin(U-POLYMER manufactured by Unitika Ltd.) were mixed at a weight ratio of 1:1 and 10% solution of this mixture in dichloroethane as a solvent was prepared. This solution was coated on the film of the carrier generation substance by an applicator to form a carrier transport layer of 20 μ in dry thickness.

Thus obtained electrophotographic photoreceptor was evaluated on its electrophotographic characteristics by the same electrostatic recording paper testing apparatus as used in Example 1 under the measuring conditions of applied voltage −6 KV, static No. 3.

The half decay exposure with white light at charging was 2.3 lux.sec which indicates very high sensitivity.

Evaluation for repeated use was conducted using the above apparatus. Change in potential by repeated use of 1000 times was examined to obtain initial potential of of −1010 V for the first time and initial potential at 1000th time of −980 V. It can be seen that reduction of potential due to repeated use was small and potential was table. Thus, excellent characteristics were exhibited.

EXAMPLES 58-61

Photoreceptors were prepared in the same manner as in Example 57 except that hydrazone compounds shown in Table 13 were used in place of the compound used in Example 57. Half decay exposure E½ (lux.sec) and initial potential $V_0$ (volt) were measured under the same measuring conditions as in Example 57 and the results are shown in Table 13. Furthermore, the photoreceptors were subjected to 1000 test cycles, each cycle comprising charging and removing of potential (removal of potential was effected by exposing to white light of 400 lux for 1 second) and initial potential $V_0$ (volt) and half decay exposure E½ are shown in Table 13.

TABLE 13

| Example | Hydrazone compound | The 1st cycle $V_0$ (volt) | The 1st cycle E½ (lux · sec) | The 1000th cycle $V_0$ (volt) | The 1000th cycle E½ (lux · sec) |
|---|---|---|---|---|---|
| 58 | III-(2) | −950 | 2.6 | −940 | 2.6 |
| 59 | III-(3) | −980 | 2.7 | −970 | 2.6 |
| 60 | III-(7) | −920 | 3.0 | −900 | 2.9 |
| 61 | III-(9) | −930 | 3.1 | −920 | 3.1 |

EXAMPLES 62-65

A bisazo pigment having the following formula was used as charge generation substance.

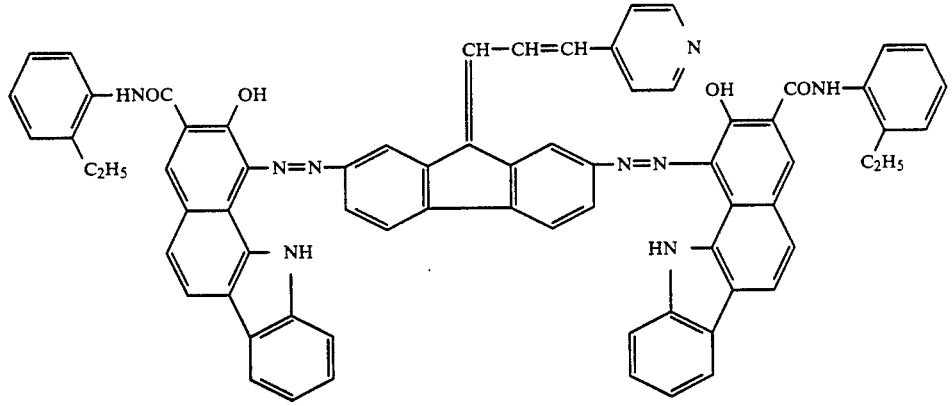

That is, 1 part by weight of this pigment and 1 part by weight of a polyester resin(BYRON 200) were mixed with 100 parts by weight of tetrahydrofuran and the mixture was dispersed together with glass beads for 2 hours by a paint conditioner apparatus. The resulting pigment dispersion was coated on the same support as used in Example 57 by an applicator to form a carrier generation layer. Thickness of this layer was about 0.2 μ.

Thereafter, carrier transport layer was formed thereon using compounds shown in Table 14 in the same manner as in Example 57 to make photoreceptors. The resulting photoreceptors were evaluated in the same manner as in Example 57. The results are shown in Table 14.

TABLE 14

| Example | Hydrazone compound | The 1st cycle $V_0$ (volt) | The 1st cycle E½ (lux · sec) | The 1000th cycle $V_0$ (volt) | The 1000th cycle E½ (lux · sec) |
|---|---|---|---|---|---|
| 62 | III-(2) | −910 | 1.5 | −870 | 1.5 |
| 63 | III-(3) | −900 | 1.6 | −870 | 1.5 |
| 64 | III-(7) | −940 | 1.9 | −930 | 1.8 |
| 65 | III-(9) | −910 | 1.9 | −900 | 1.8 |

What is claimed is:

1. An electrophotographic photoreceptor which comprises an electroconductive support and, provided thereon, a photosensitive layer which contains a hydrazone compound represented by the following formula [I], [II], or [III]:

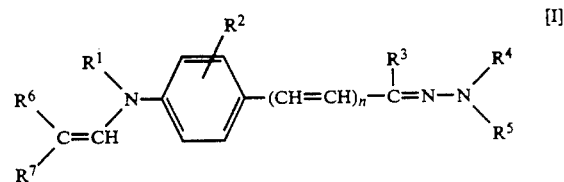

wherein $R^1$ represents an alkyl group which may have substituent, an aralkyl group which may have substituent, an aryl group which may have substituent, a heterocyclic ring group which may have substituent or a group of atoms necessary to form a ring together with nitrogen atom carrying $R^1$ and carbon atom in the ortho position of the benzene ring in respect to said nitrogen atom; $R^2$ represents a hydrogen atom, an alkyl group which may have substituent, or an alkoxy group which may have substituent; $R^3$ represents a hydrogen atom, an alkyl group which may have substituent or an aryl group which may have substituent; $R^4$ represents an alkyl group which may have substituent, an aralkyl group which may have substituent or an aryl group which may have substituent; $R^5$ represents an alkyl group which may have substituent, an aralkyl group which may have substituent, an aryl group which may have substituent or an alkenyl group which may have substituent; $R^6$ and $R^7$ which may be identical or different each represents a hydrogen atom, an alkyl group which may have substituent, an aralkyl group which may have substituent or aryl group which may have substituent and $R^6$ and $R^7$ may link to each other to form a ring; and n represents 0 or 1,

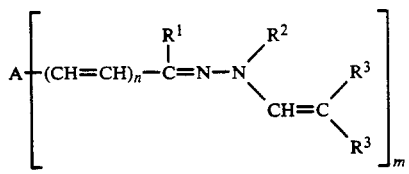

wherein A represents an aromatic ring or a heterocyclic ring, $R^1$ represents a hydrogen atom, an alkyl group which may have substituent or an aryl group which may have substituent; $R^2$ represents an alkyl group which may have substituent, an aralkyl group which may have substituent or an aryl group which may have substituent; $R^3$ and $R^4$ which may be identical or different each represents a hydrogen atom, an alkyl group which may have substituent, an aralkyl group which may have substituent or aryl group which may have substituent and $R^3$ and $R^4$ may link to each other to form a ring; m represents 1 or 2; and n represents 0 or 1,

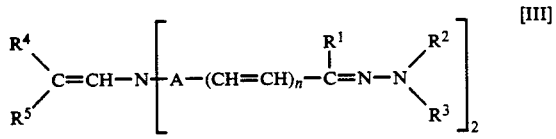

wherein A represents an aromatic ring and the two A may link through a bond, an atom or a group of atoms to form a heterocyclic ring together with nitrogen atom, $R^1$ represents a hydrogen atom, an alkyl group which may have substituent or an aryl group which may have substituent; $R^2$ and $R^3$ which may be identical or different each represents an alkyl group which may have substituent, an aralkyl group which may have substituent or an aryl group which may have substituent; $R^4$ and $R^5$ which may be identical or different each represents a hydrogen atom, an alkyl group which may have substituent, an aralkyl group which may have substituent or aryl group which may have substituent and $R^4$ and $R^5$ may link to each other to form a ring; and n represents 0 or 1.

2. An electrophotographic photoreceptor according to claim 1, wherein the photosensitive layer contains the hydrazone compound dissolved or dispersed in a binder resin.

3. An electrophotographic photoreceptor according to claim 1, wherein the photosensitive layer contains the hydrazone compound and a carrier generation material.

4. An electrophotographic photoreceptor according to claim 1, wherein the photosensitive layer comprises a carrier generation layer and a carrier transport layer, said carrier transport layer containing the hydrazone compound.

5. An electrophotographic photoreceptor according to claim 4, which has the carrier generation layer on the support and the carrier transport layer on the carrier generation layer.

6. An electrophotographic photoreceptor according to claim 2, wherein amount of the binder resin is 0.2–10 times the weight of the hydrazone compound.

7. An electrophotographic photoreceptor according to claim 6, wherein the amount of the binder resin is 0.5–5 times the weight of the hydrazone compound.

8. An electrophotographic photoreceptor according to claim 1, wherein the electroconductive support is selected from the group consisting of metal drum, metal sheet and sheet-like, drum-like and belt-like paper and plastic film subjected to electroconductive treatment.

9. An electrophotographic photoreceptor according to claim 2 which is for a lithographic printing plate and wherein the binder resin is an alkali-soluble resin.

* * * * *